(12) United States Patent
Greenwood et al.

(10) Patent No.: US 6,878,544 B2
(45) Date of Patent: Apr. 12, 2005

(54) RETINAL CELL LINES WITH EXTENDED LIFE-SPAN AND THEIR APPLICATIONS

(75) Inventors: John Greenwood, London (GB); Peter Adamson, Bampton (GB); Raymond Lund, Salt Lake City, UT (US); Weng Tao, Lincoln, RI (US)

(73) Assignee: Neurotech SA, Evry (FR)

( * ) Notice: Subject to any disclaimer, the term of this patent is extended or adjusted under 35 U.S.C. 154(b) by 5 days.

(21) Appl. No.: 09/559,707

(22) Filed: Apr. 27, 2000

(65) Prior Publication Data

US 2003/0059868 A1 Mar. 27, 2003

Related U.S. Application Data

(63) Continuation-in-part of application No. 09/182,516, filed on Oct. 30, 1998, now Pat. No. 6,090,624, which is a continuation-in-part of application No. 08/973,553, filed as application No. PCT/FR97/00709 on Apr. 18, 1997, now Pat. No. 6,183,735.

(30) Foreign Application Priority Data

Apr. 19, 1996 (FR) .............................. 96 04964

(51) Int. Cl.$^7$ .............................. C12N 5/10; C12N 5/06
(52) U.S. Cl. ....................................... 435/353; 435/325
(58) Field of Search ................................ 435/325, 353, 435/70.3, 440, 455; 424/93.21; 514/44

(56) References Cited

U.S. PATENT DOCUMENTS 5,998,598 A * 12/1999 Csaky et al.
6,090,624 A * 7/2000 Greenwood et al.
6,183,735 B1 * 2/2001 Greenwood et al.
6,361,771 B1 * 3/2002 Tao et al.

FOREIGN PATENT DOCUMENTS

WO    WO 97/19694    6/1997
WO    WO 97/40139    10/1997
WO    WO 00/10580    3/2000

OTHER PUBLICATIONS

Dunn et al (1996) Exp. Eye Res. 62: 155–169.*
Dutt et al (1990) Oncogene 5:195–200.*
Litchfield et al (1997) Exp. Eye Res. 64: 655–666.*
Manuelli et al (1995) Diab. Nutr. Metab. 8: 281–291.*
Verma et al (1997) Nature 389: 239–242.*
Anderson (998) Nature 392: 25–30.*
Fox (2000) ASM News, vol. 66 (2): 1–3.*
Bodnar et al (1998) Science 279:349–352.*
Dunn et al (1998) Invest Ophthalmol Vis Sci 39:2744–2749.*
Winton et al. (2000). *IOVS 41*: S857.
Dunaief et al. (1995). *Human Gene Therapy 6*: 1225–1229.
Greenwood et al. (1996). *SV40 71* 0165–5728.
Dutt et al. (1990). *ONCOGENE 5* 0950–9232.

International Search Report for PCT/IB01/00860 mailed Oct. 8, 2002.
Byun et al., 1996. "Analysis of the relative level of gene expression from different vectors used for gene therapy." Gene Ther. 3: 780–8.
Kim et al., 1998. "Construction of retroviral vectors with improved safety, gene expression, and versatility." J Virol. 72: 994–1004.
McGuire et al., 1987. "Isolation of rat aortic endothelial cells by primary explant techniques and their phenotypic modulation by defined substrata." Lab Invest. 57: 94–105.
Greenwood et al., 1993. "Lymphocyte migration through endothelial cell monolayers derived the blood–retinal barrier." Immunology. 80: 401–6.
Greenwood, 1992. "Characterization of a rat retinal endothelial cell culture and the expression of glycoprotein in brain and retinal endothelium in vitro." J Neuroimmunol. 39: 123–32.
Abbott et al., 1992. "Development and characterisation of a rat capillary endothelial culture: towards an in vitro blood–brain barrier." J Cell Sci. 103: 23–37.
Jat et al., 1986. "Recombinant retroviruses encoding simian virus 40 T antigen and polyomavirus large and middle T antigens." Mol Cell Biol. 6(4): 1204–17.
Chang et al., 1991. "An improved method for isolation and culture of pigment epithelial cells from retina." Curr Eye Res. 10: 1081–1086.
Neill & Barnstable, 1990. "Expression of the cell surface antigens RET–PE2 and N–CAM by rat retinal pigment epithelial cells during development and in tissue culture." Exp Eye Res. 51: 573–83.
Cotten et al., 1994. "Lipopolysaccharide is a frequent contaminant of plasmid DNA preparations and can be toxic to primary human cells in the presence of adenovirus." Gene Ther. 1: 239–46.
Remy et al., 1994. "Gene transfer with a series of lipophilic DNA–binding molecules." Bioconjugafe Chem. 5: 647–54.

(Continued)

*Primary Examiner*—David Guzo
(74) *Attorney, Agent, or Firm*—Mintz, Levin, Cohn, Ferris, Glovsky and Popeo, P.C.; Ivor R. Elrifi, Esq.; Christina K. Stock, Esq.

(57) ABSTRACT

The invention features retina-derived (retinal endothelial or retinal epithelial pigment) cell lines with extended life-span and capable of being implanted in the retina and of carrying a therapeutic substance to the eye and to the central nervous system. Such lines can also be used as a model for studying blood central nervous system interfaces. These lines are derived from primary retinal cultures selected from the group consisting of primary retinal endothelial cells and primary retinal epithelial cells, comprise a polynucleotide containing an oncogene, which polynucleotide is optionally associated with at least one selection gene, and have the morphological characteristics and at least the expression characteristics of the surface antigens of corresponding primary cultures.

1 Claim, 35 Drawing Sheets

OTHER PUBLICATIONS

Rahmani et al., 1996. "The cause–specific prevalence of visual impairment in an urban population. The Baltimore Eye Survey." Ophthalmology. 103: 1721–6.

Zarbin, 1998. "Age–related macular degeneration: review of pathogenesis." Eur J Ophthalmol. 8: 199–206.

de Juan et al., 1998. "Translocation of the retina for management of subfoveal choroidal neovascularization II: a preliminary report in humans." Am J Ophthalmol. 125: 635–46.

Lewis et al., 1999. "Macular translocation for subfoveal choroidal neovascularization in age–related macular degeneration: a prospective study." Am J Ophthalmol. 128: 135–46.

Lund et al., 1997. "Intraretinal transplantation to prevent photoreceptor degeneration." Ophtalmic Res. 29: 305–19.

Li & Turner, 1988. "Inherited retinal dystrophy in the RCS rat: prevention of photoreceptor degeneration by pigment epithelial cell transplantation." Exp Eye Res. 47:911–7.

Lopez et al., 1989. Transplanted retinal pigment epithelium modifies the retinal degeneration in the RCS rat. Invest Ophthalmol Vis Sci. 30: 586–8.

Liz & Turner, 1991. "Optimal conditions for long–term photoreceptor cell rescue in RCS rat: the necessity for healthy RPE transplants." Exp Eye Res. 52: 669–79.

Dunn et al., 1996. "ARPE–19, a human retinal pigment epithelial cell line with differentiated properties." Exp Eye Res. 62: 155–69.

Cowey & Franzini, 1979. "The retinal origin of uncrossed optic nerve fibres in rats and their role in visual discrimination." Exp Brain Res. 35: 443–55.

Massof & Fenkelstein, 1979. "Rod sensitivity relative to cone sensitivity in retinitis pigmentosa." Invest Ophthalmol Vis Sci. 18: 26–72.

Niederkorn, 1990. "Immune privilege and immune regulation in the eye." Adv. Immunol. 48: 191–226.

Jiang et al., 1994. "Immunologic consequences of intraocular implantation of retinal pigment epithelial allografts." Exp Eye Res. 58: 719–28.

Villegas–Perez et al., 1998. "Ganglion cell loss in RCS rat retina: a result of compression of axons by contracting intraretinal vessels linked to the pigment epithelium." J Comp Neurol. 392: 58–77.

Zhang & Bok, 1998. "Transplantation of retinal pigment epithelial cells and immune response in the subretinal space." Ophthamol Vis Sci. 39: 1021–7.

Algvere et al., 1994. "Transplantation of fetal retinal pigment epithelium in age–related macular degeneration with subfoveal neovascularization." Graefe's Arch Clin Exp Ophthalmol. 232: 707–16.

Algvere et al., 1997. "Transplantation of RPE in age–related macular degeneration: observations in disciform lesions and dry RPE atrophy." Graefe's Arch Clin Exp Ophthalmol. 235: 149–58.

Dunn et al., 1998. "Use of the ARPE–19 cell line as a model of RPE polarity: basolateral secretion of FGF5." Invest Ophthalmol. Vis. Sci. 39: 2744–9.

Finnemann et al., 1997. "Phagocytosis of rod outer segments by retinal pigment epithelial cells require (v)beta5 integrin for binding but not for internalization." Proc Natl Acad Sci USA 94: 12932–7.

Handa et al., "The advanced glycation endproduct pentosidine induces the expression of PDGF–B in human retinal pigment epithelial cells." Exp Eye Res. 66: 411–9.

Holtkamp et al., "Polarized secretion of IL–6 and IL–8 by human retinal pigment epithelial cells." Clin Exp Immunol. 112: 34–43.

Maidji et al., 1996. "Accessory human cytomegalovirus glycoprotein US9 in the unique short component of the viral genome promotes cell–to–cell transmission of virus in polarized epithelial cells." J Virol. 70: 8402–10.

McGuire & Orkin, 1987. "Isolation of rat aortic endothelial cells by primary explant techniques and their phenotypic modulation by defined substrata." Lab Invest. 57(1): 94–105.

Hammang et al., 1990. "Immortalized retinal neurons derived from SV40 T–antigen–induced turmors in transgenic mice." Neuron. 4(5):775–782.

Dutt et al., 1994. "Establishment of human retinal cell line by transfection of SV40 T antigen gene with potential to undergo neuronal differentiation." DNA and Cell Biol. 13(9):909–921.

Dutt et al., 1996. "Proto–oncogene expression in cAMP and TPA–mediated neuronal differentiation in a human retinal cell line KGLDMSM." Curr. Eye Res. 15(5):377–485.

* Frederiksen et al., 1988. "Immortalization of precursor cells from the mammalian CNS." Neuron. 1: 439–48.

* Chou, 1989. "Differentiated mammalian cell lines immortalized by temperature–sensitive tumor viruses." Mol Endocrinol. 3: 1511–4.

* Dutt et al., 1990. "Establishment of human retinal pigment epithelial cell lines by oncogenes." Oncogene. 5: 195–200.

* Wang et al., 1993. "Lymphocyte adhesion to cultured endothelial cells of the blood–retinal barrier." J Neuroimmunol. 48: 161–8.

* Lloyd, 1997. "Modifying the drug discovery/drug development paradigm." 2(10):397–8.

* Greenwood et al., 1995. "SV40 large T immortalised cell lines of the rat blood–brain and blood–retinal barrier retain their phenotypic and immunological characteristics." J Neuroimmunol. 71: 51–63.

* Kawasaki et al., 1995. Invest Ophthalmol Vis Sci. 36(4): pS550.

* cited by examiner

WO 97/40139          No de la demande internationale: PCT/FR97/00709

MICRO-ORGANISMES
Feuille facultative relative au micro-organisme mentionné au page 4 ligne 15 de la description

A. IDENTIFICATION DU DEPOT

Collection Nationale de Cultures de Micro-organismes

Adresse de l'institution de dépôt (y compris le code postal et le pays)

28 rue du Docteur Roux, 75724 PARIS CEDEX 15

| Date du dépôt  18 avril 1996 | N° d'ordre  I-1694 |
|---|---|

B. INDICATIONS SUPPLÉMENTAIRES (à ne remplir que si nécessaire). Une feuille séparée est jointe pour la suite de ces renseignements ☐

"En ce qui concerne les désignations dans lesquelles un brevet européen est demandé, un échantillon du micro-organisme déposé ne ser accessible, jusqu'à la publication de la mention de la délivrance du brevet européen ou jusqu'à la date à laquelle la demande sera rejetée, retirée ou réputée retiré, que par la remise d'un échantillon à un expert désigné par le requérant. (règle 28.4) de la CBE)".

C. ÉTATS DÉSIGNÉS POUR LESQUELS LES INDICATIONS SONT DONNEES (si les indications ne sont pas données pour tous les États désignés)

EUROPE            NOUVELLE-ZELANDE
AUSTRALIE         ETATS-UNIS D'AMERIQUE
CANADA
JAPON

D. INDICATIONS FOURNIES SÉPARÉMENT (à ne remplir que si nécessaire)

Les indications énumérées ci-après seront soumises ultérieurement au Bureau International (spécifier la nature générale des indications p. ez., "No d'ordre du dépôt")

E. ☐ La présente feuille à été reçue avec la demande internationale lorsque celle-ci a été déposée (à vérifier par l'office récepteur)

_____
(Fonctionnaire autorisé)

☐ Date de réception (en provenance du déposant) par le Bureau International

C. BEDNARICK
_____
(Fonctionnaire autorisé)

Formulaire PCT/RO/134 (Janvier 1981)

Fig. 18

WO 97/40139　　　　　　　　　　　　No de la demande internationale: PCT/FR97/00709

| MICRO-ORGANISMES |
|---|
| Feuille facultative relative au micro-organisme mentionné au page 4 ligne 11 de la description |

A. IDENTIFICATION DU DÉPÔT

Collection Nationale de Cultures de Micro-organismes

Adresse de l'institution de dépôt (y compris le code postal et le pays)

28 rue du Docteur Roux, 75724 PARIS CEDEX 15

| Date du dépôt 18 avril 1996 | N° d'ordre I-1695 |
|---|---|

B. INDICATIONS SUPPLÉMENTAIRES (à ne remplir que si nécessaire). Une feuille séparée est jointe pour la suite de ces renseignements ☐

"En ce qui concerne les désignations dans lesquelles un brevet européen est demandé, un échantillon du micro-organisme déposé ne ser accessible, jusqu'à la publication de la mention de la délivrance du brevet européen ou jusqu'à la date à laquelle la demande sera rejetée, retirée ou réputée retiré, que par la remise d'un échantillon à un expert désigné par le requérant. (règle 28.4) de la CBE)".

C. ÉTATS DÉSIGNÉS POUR LESQUELS LES INDICATIONS SONT DONNÉES (si les indications ne sont pas données pour tous les États désignés)

EUROPE　　　　　　　　NOUVELLE-ZELANDE
AUSTRALIE　　　　　　ETATS-UNIS D'AMERIQUE
CANADA
JAPON

D. INDICATIONS FOURNIES SÉPARÉMENT (à ne remplir que si nécessaire)

Les indications énumérées ci-après seront soumises ultérieurement au Bureau international (spécifier la nature générale des indications p. ez., "No d'ordre du dépôt")

E. ☐ La présente feuille à été reçue avec la demande internationale lorsque celle-ci a été déposée (à vérifier par l'office récepteur)

_____
(Fonctionnaire autorisé)

☐ Date de réception (en provenance du déposant) par le Bureau International

C. BEDNARICK
_____
(Fonctionnaire autorisé)

Formulaire PCT/RO/134 (Janvier 1981)

Fig. 19

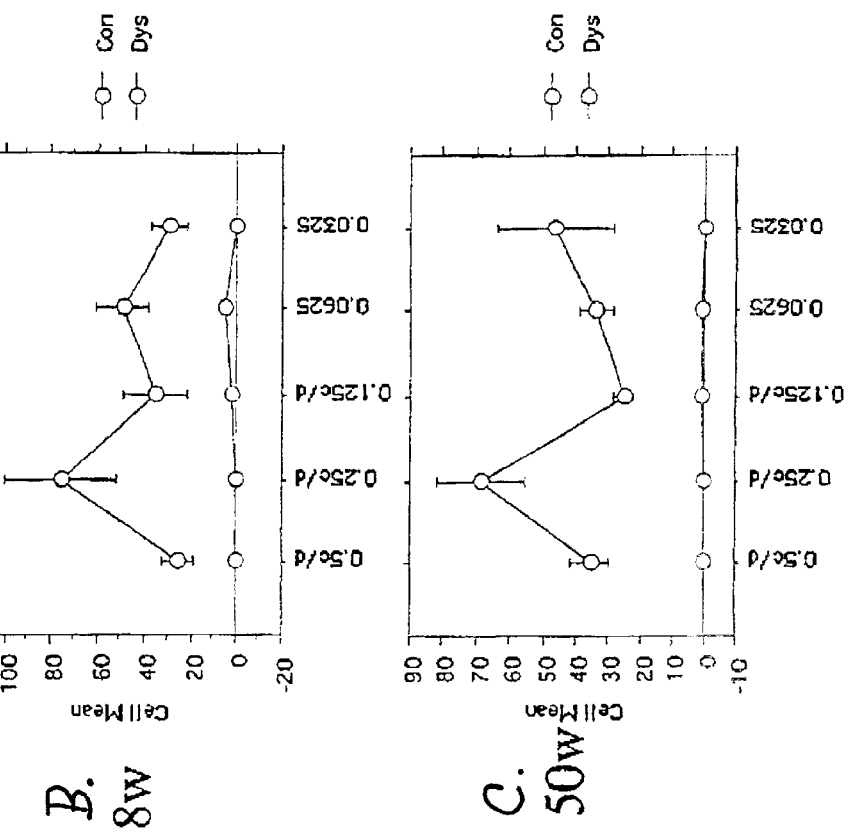
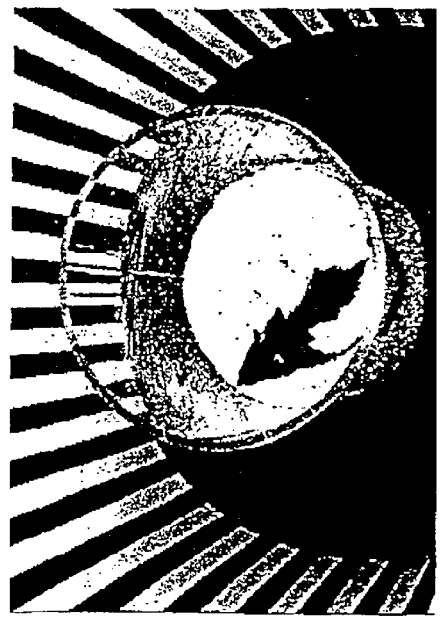
FIGURE 20
Optokinetic performance in RCS rats at 8-50 weeks of age control
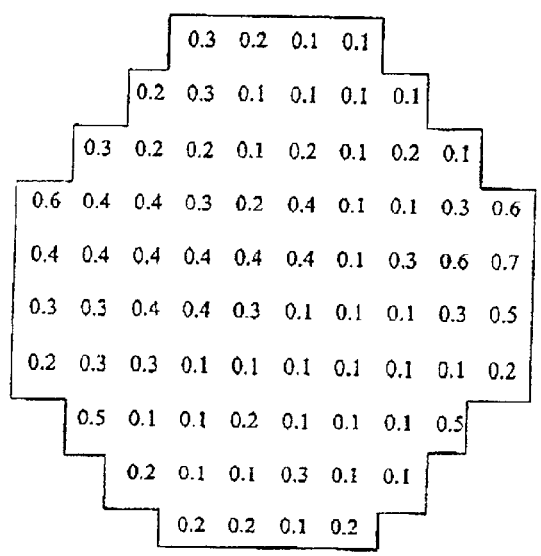
sham
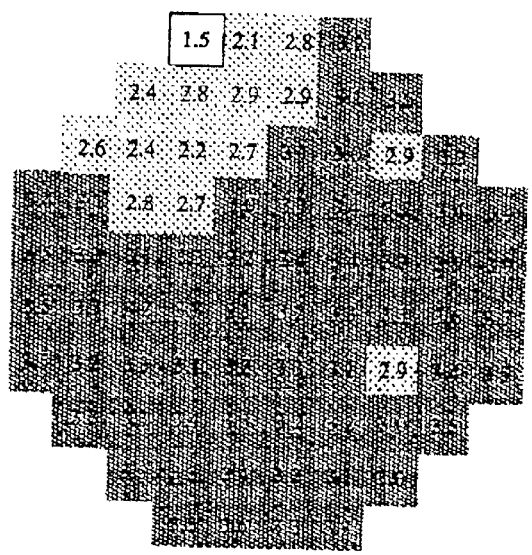
LD7.4 #1
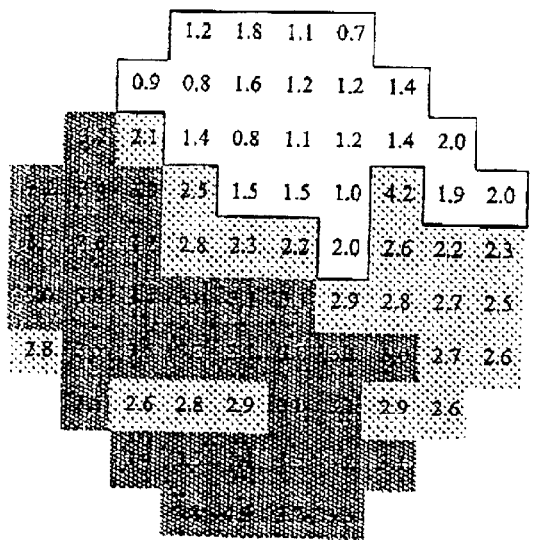
LD7.4 #2
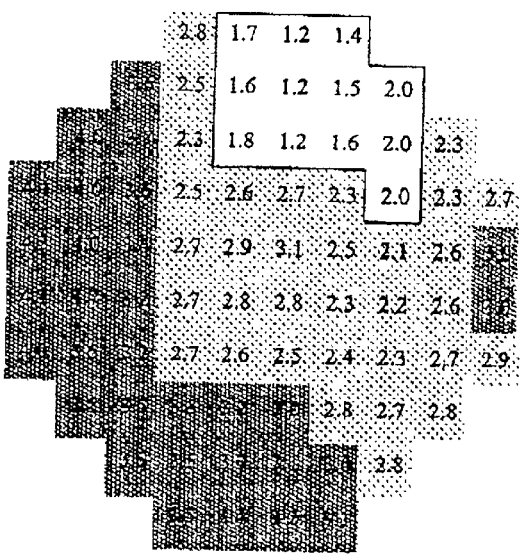
FIGURE 22

Optokinetic performance in RCS rats with Human RPE cell transplants 116 and 7
A.
- At 7 weeks of age (approx. 3-4 weeks post trasnplantation)
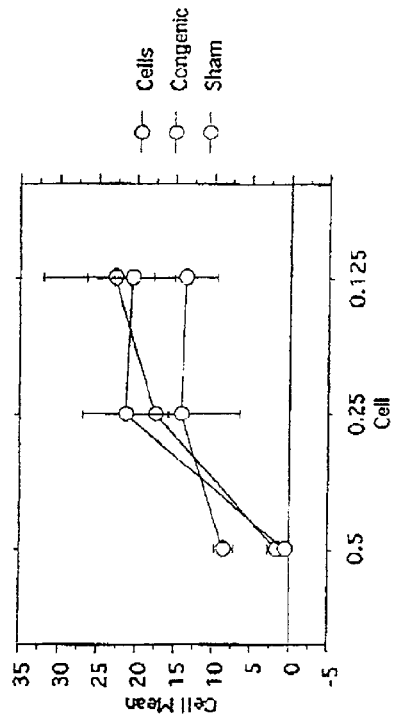
B.
- At 14 weeks of age (approx. 10-11 weeks post trasnplantation)
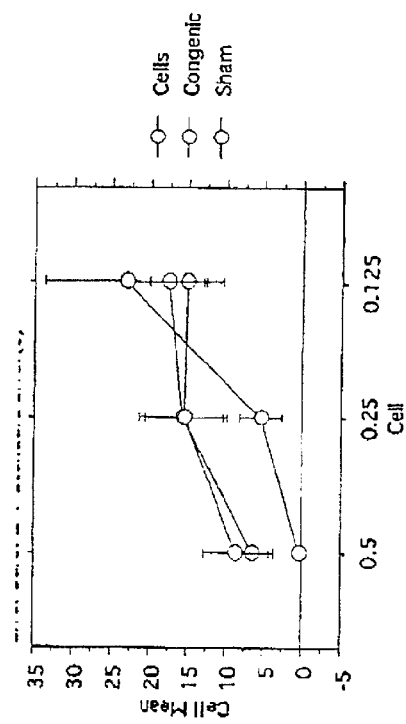
FIGURE 23

A
B
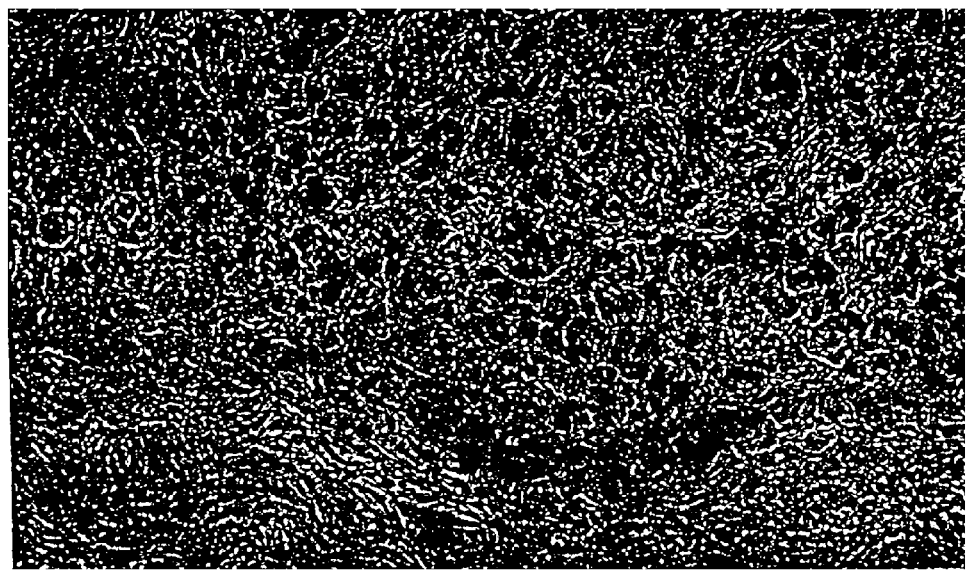
FIGURE 25

A
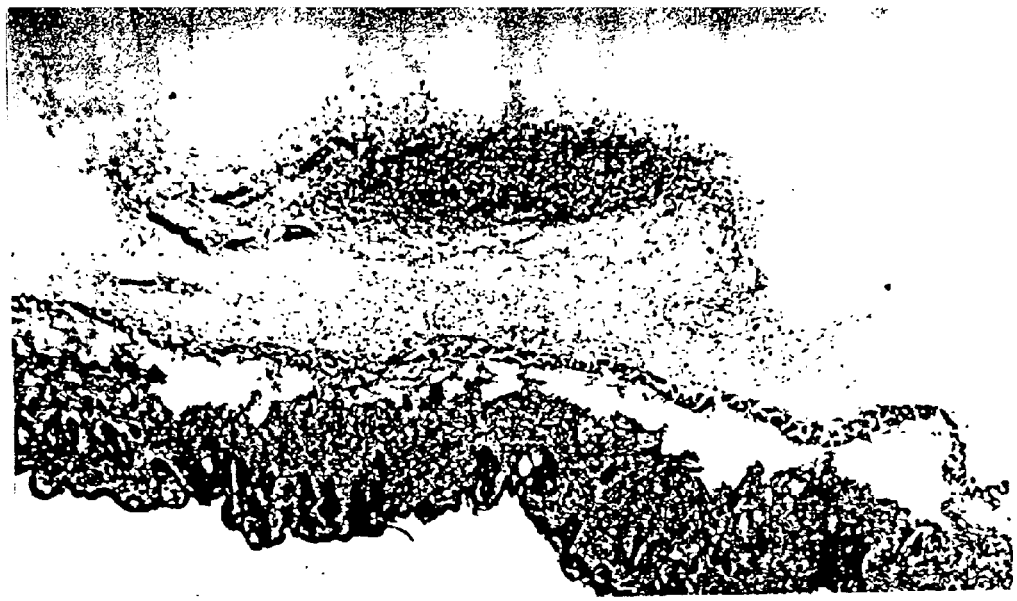
B
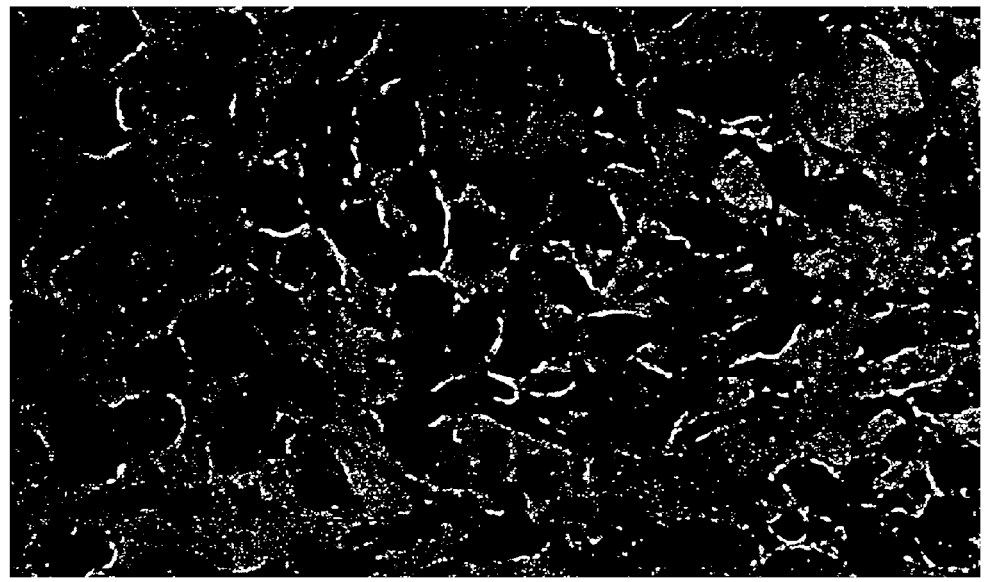
FIGURE 26

A
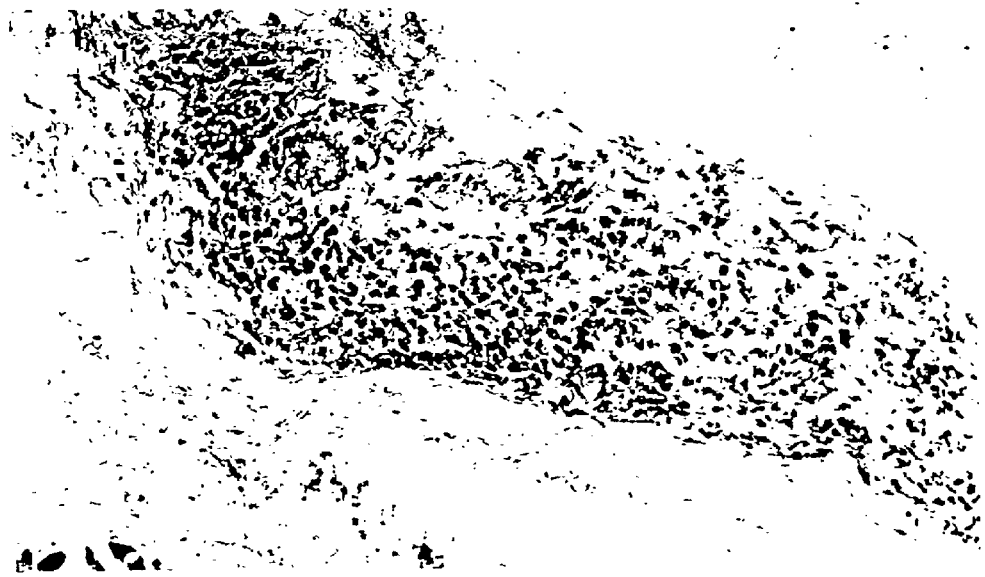
B
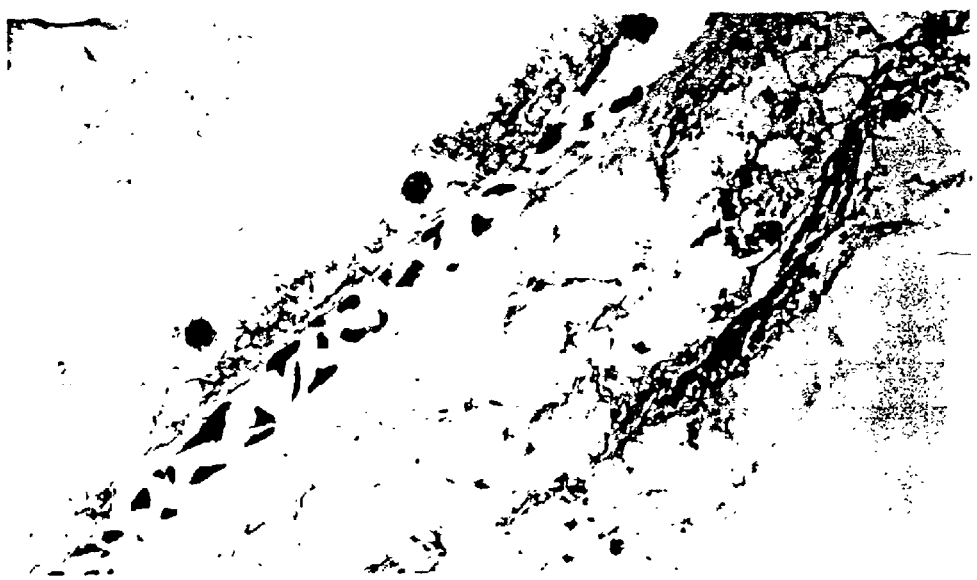
FIGURE 27

A: Head tracking apparatus as viewed from above.
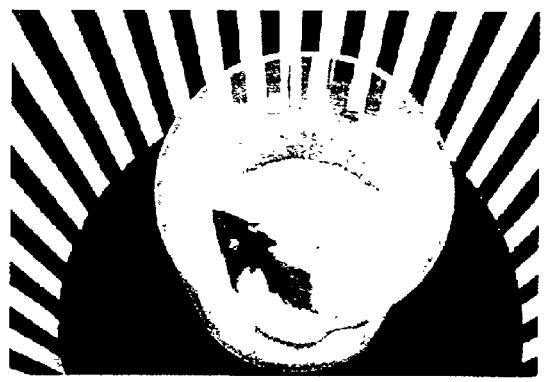
B: Head tracking 10 weeks postoperative.
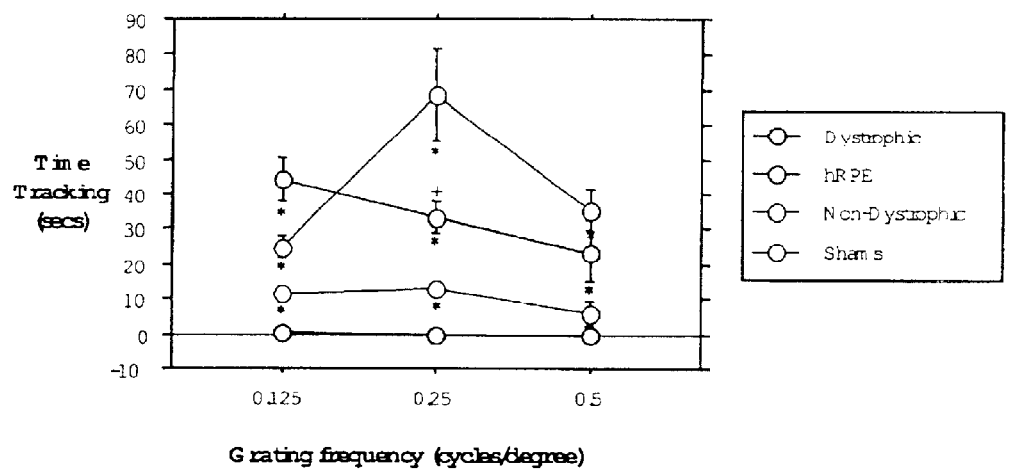
C: Head tracking 20 weeks postoperative.
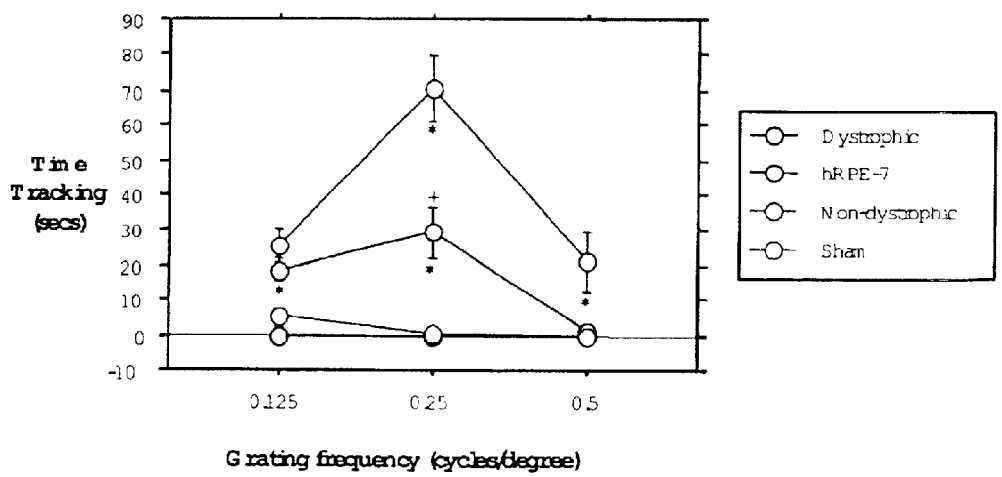
FIG. 29

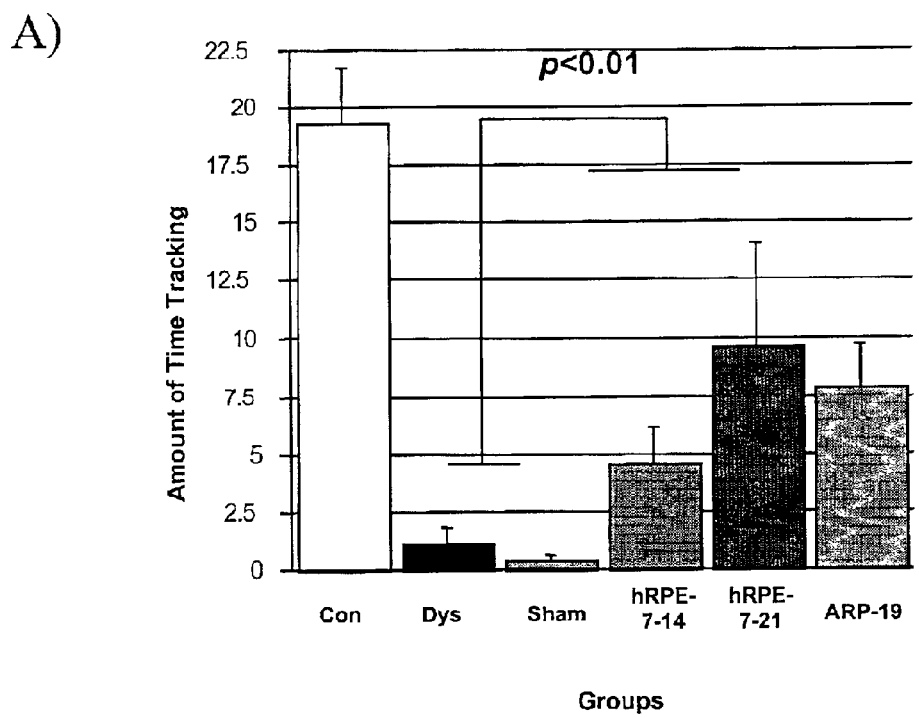
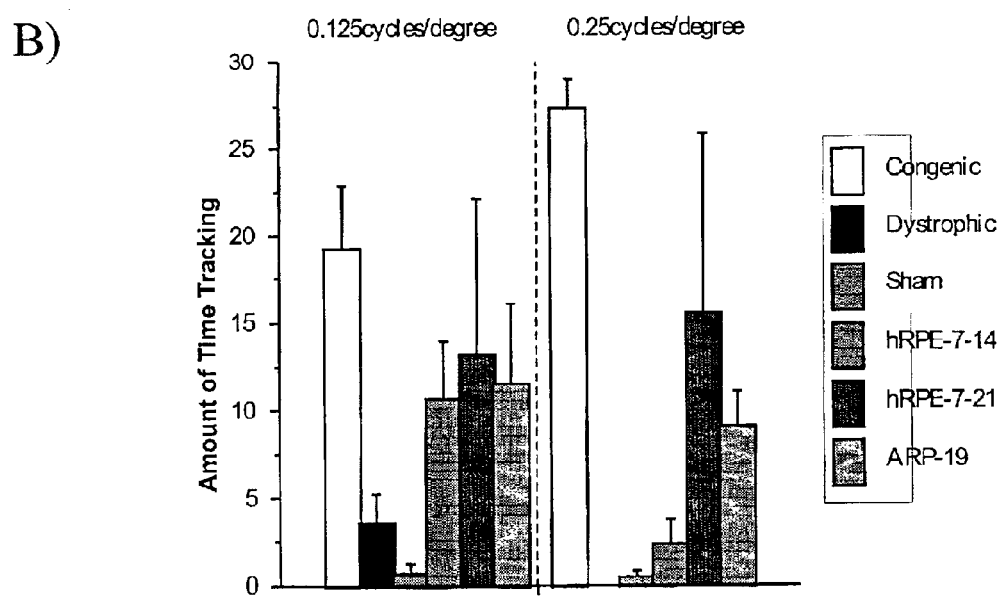
FIG. 32

RETINAL CELL LINES WITH EXTENDED LIFE-SPAN AND THEIR APPLICATIONS

CLAIM OF PRIORITY

This application is a continuation-in-part of U.S. patent application Ser. No. 09/182,516, filed Oct. 30, 1998, now U.S. Pat. No. 6,090,624, which is a continuation-in-part of U.S. patent application Ser. No. 08/973,553, filed Jan. 22, 1998, now U.S. Pat. No. 6,183,735, which is the United States national stage of PCT International patent application PCT/FR97/00709, filed Apr. 18, 1997, published as WO 97/40139 on Oct. 30, 1997, which claims priority to French patent application 96/04964, filed Apr. 19, 1996.

TECHNICAL FIELD OF THE INVENTION

The present invention relates to novel cell lines with extended life-span of retinal origin (retinal endothelial and retinal pigment epithelial origin) that are capable of being implanted in the retina and of conveying a substance of therapeutic interest into the eye or the central nervous system.

BACKGROUND OF THE INVENTION

Both the blood-brain barrier and the blood-retina barrier are important in controlling the passage of substances to and from the neural parenchyma, especially in the maintenance of homeostasis.

In the retina, the blood-retina barrier is composed of two different types of anatomically separate cells. The retinal vascular endothelium, which supplies the anterior portion of the retina, is currently considered to have an identical structure to the cerebral endothelium (Towler et al., 480 J. Physiol. 10–11P (1994)), whereas the cells of the retinal pigment epithelium cover the permeable vessels of the choroidal circulation and form the posterior barrier by means of their tight apical junctions. Retinal pigment epithelium (RPE) cells are consequently similar to the tight junction epithelial cells of the choroid plexus.

The cerebral and retinal endothelia are of a different nature from the peripheral endothelium. The cells of these epithelia do not serve only to express tight junctions and form a physical barrier. Other properties of the endothelium contribute to the specialized nature of this barrier, such as the distribution and expression of substances such as the glucose transporter (GLUT-1), the transferrin receptor, and P-glycoprotein (Pgp), the expression product of the drug resistance gene. The cerebral and retinal endothelia also differ from the peripheral endothelium in their permeability to the circulating leukocytes.

For in vivo transfer, the use of primary nerve tissues of fetal origin for cellular transplantation in human therapy gives rise to numerous ethical and practical problems. One alternative to this problem is to use primary cell lines of neural origin (e.g., neurons, glial cells, astrocytes) or non-neural cell lines (e.g., fibroblasts, myoblasts, chromaffin cells of the adrenal medulla, hepatocytes). Although the cell lines of the adrenal medulla, fibroblasts or myoblasts can actually release active substances in vivo, such cells are not normally present in the neuroretina of the central nervous system (CNS). Such cells can modify the normal function of the nervous system and cause a rejection reaction.

Because of the heterogeneity of the endothelial cells of different tissues, influenced by the environment of these cells, it is important to be able to have cells adapted to the retinal environment in order to have tools permitting a good morphological and physiological integration of the cells when the cells are implanted or grafted.

SUMMARY OF THE INVENTION

The invention provides lines of cells with extended life-span derived from primary cultures of the endothelium of the blood-retina barrier and the retinal pigment epithelium of mammals. These lines of cell are better capable of meeting practical needs, especially in that all the lines obtained are stable and have most of the characteristics of the differentiated cells.

The invention provides mammalian cell lines ("cell lines") with extended life-span, characterized
  (a) in that they are derived from primary cultures of retinal cells selected from the group comprising the primary retinal endothelial cells and the primary retinal epithelial cells,
  (b) in that they comprise a polynucleotide containing a heat-sensitive viral oncogene, and which polynucleotide may be associated with at least one selection gene, and
  (c) in that they stably exhibit the morphological characteristics and at least the surface antigen expression characteristics of the corresponding primary culture cells. Stability is understood as meaning the maintenance of the phenotypic characteristics of the lines with extended life-span for up to the $52^{nd}$ passages.

The invention also provides cell lines derived from the lines with extended life-span as defined above ("vector lines"), characterized
  (a) in that they comprise at least one cell line as defined above, associated with an expression vector comprising a sequence coding for a polypeptide, a protein, or a viral vector, optionally associated with at least one selection gene, and optionally associated with at least one marker gene, and
  (b) in that they are capable, in vivo, of integrating into the retina and especially the subretinal space of a host mammal, preventing the loss of photoreceptors and producing the peptide, the protein or the viral vector.

An "expression vector" is any polypeptide integrated into the genome or present in the cytoplasm of the cell lines that can permit the production of polypeptide, protein, or viral vector.

The invention further provides a model for studying and identifying the biochemical and cellular systems of the blood-retina barrier, characterized in that it comprises at least one cell line as defined above.

The invention also provides cell lines with extended life-span, deriving from primary cultures of retinal pigment epithelial cell lines of mammals including humans, the cell lines being modified by a polynucleotide containing a non-thermosensitive viral or cellular oncogene, the cells being capable, in vivo, of integrating into the retina, the cells not being tumorigenic in vivo. The polynucleotide containing the oncogene may be associated with at least one selection gene.

The invention also provides cell lines with extended life-span, derived from primary cultures of retinal pigment epithelial cell lines of mammals including humans, the cell lines being modified by a polynucleotide containing the human telomerase reverse transcriptase (hTRT) gene or a sequence able to activate the human telomerase reverse transcriptase endogenous gene, the cells being capable, in vivo, of interacting with retinal cells, the cells not being tumorigenic in vivo. The polynucleotide containing the hTRT gene or the sequence able to activate the hTRT endogenous gene may be associated with at least one selection gene.

The expression vector can be associated with at least one selection gene and optionally at least one marker gene. The expression vector is driven by strong viral promoters, cell-specific promoters, house-keeping gene promoters, inducible promoters, or hybrid promoters. Therapeutic proteins that can be expressed by the cells are, for instance, trophic factors or anti-apoptotic factors, immunomodulating peptides, immunoprotective peptides, protease inhibitors, angiogenic anti-angiogenic peptides, cytokines, prodrug converting enzymes or viral suicide genes, superoxide dismutase, or free radical scavengers.

The invention also provides a method for treating primary and secondary ophthalmologic or neurological disorders such as retinal degradation, diabetic retinopathy, eye and retinal inflammation, eye and retinal primary and secondary tumors, neurological degenerative disorders, neuronal degeneration, and brain tumors, the method comprising grafting mammalian retinal pigment epithelial cell lines derived from primary cultures and modified by insertion of a polynucleotide containing a non-thermosensitive viral or cellular oncogene, the cells can integrate in vivo into the retina the cells not being tumorigenic in vivo.

BRIEF DESCRIPTION OF THE DRAWINGS

FIG. 18 is an identification of the deposit of the retinal pigment epithelial cells with extended life-span called IO/LD7/4 on 18th Apr. 1996 in the Collection Nationale de Cultures de Micro-organismes (CNCM) held by the Institut Pasteur, 28 rue de Docteur Roux, 75724 PARIS CEDEX 15, under the identification no. I-1694. The indications in section B states (in French):

With regard to the nominations in which a European patent is applied for, until the publication of the mention of the grant of the European patent or until the date on which the application shall be refused or withdrawn or shall be deemed to be withdrawn, a sample of the deposited microorganism shall be available only by the issue of a sample to an expert nominated by the requester (Rule 28.4) of the EPC).

FIG. 19 is an identification of the deposit of the retinal endothelial cells with extended life-span called IO/JG2/1 on 18th Apr. 1996 in the Collection Nationale de Cultures de Micro-organismes held by the Institut Pasteur, 28 rue de Docteur Roux, 75724 PARIS CEDEX 15, under the identification no. I-1695. The indications in section B states (in French):

With regard to the nominations in which a European patent is applied for, until the publication of the mention of the grant of the European patent or until the date on which the application shall be refused or withdrawn or shall be deemed to be withdrawn, a sample of the deposited microorganism shall be available only by the issue of a sample to an expert nominated by the requester (Rule 28.4) of the EPC).

FIGS. 20A–C are a pictograph and a set of graphs showing the head tracking in RCS dystrophic (dys) and non-dystrophic rats (con) at 8 weeks (8w; FIG. 20B) and 50 weeks of age (50w; FIG. 20C). The ordinate is a measure of time spent tracking to the revolving drum (FIG. 20A).

Figure 21:
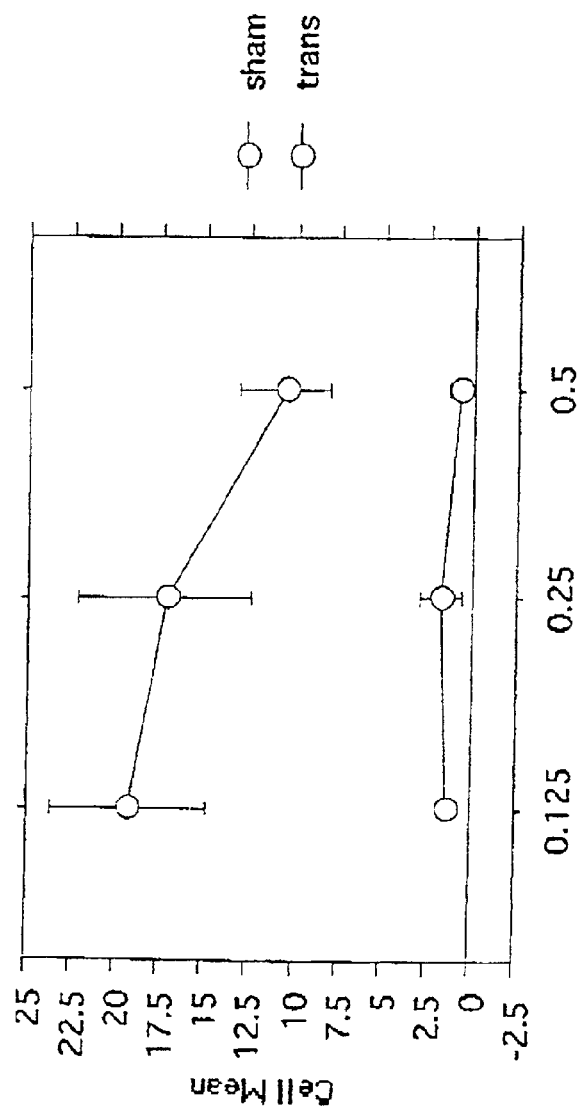

FIG. 21 is a graph showing the tracking behavior in dystrophic ROS rats to stripes of different width. The shams perform near baseline. The cell transplanted rats show significant spared performance.

FIG. 22 is a set of recordings of elevation of luminance over baseline in a set of animals. Each record shows responses at points 200 $\mu$m apart across the superior colliculus (dorsal retinal representation above, temporal to left). Unshaded show responses equal to or less than 2.0 candela/m$^2$; light shading 2.1–2.9 and dark shading >2.9. Animals were tested at 5 months post operative. As can be seen, there is a small sham effect around the injection site, but significantly greater preservation after cell grafting.

FIGS. 23A–B are a set of graphs showing the head tracking after human cell line grafts at 7 weeks (FIG. 23A) and 14 weeks of age (FIG. 23B). Note that the cell transplanted dystrophic rats (cells) perform much like non-dystrophics (congenic) by 10–11 weeks (FIG. 23B) post-transplantation and are significantly improved over sham-injected rats.

Figure 24:
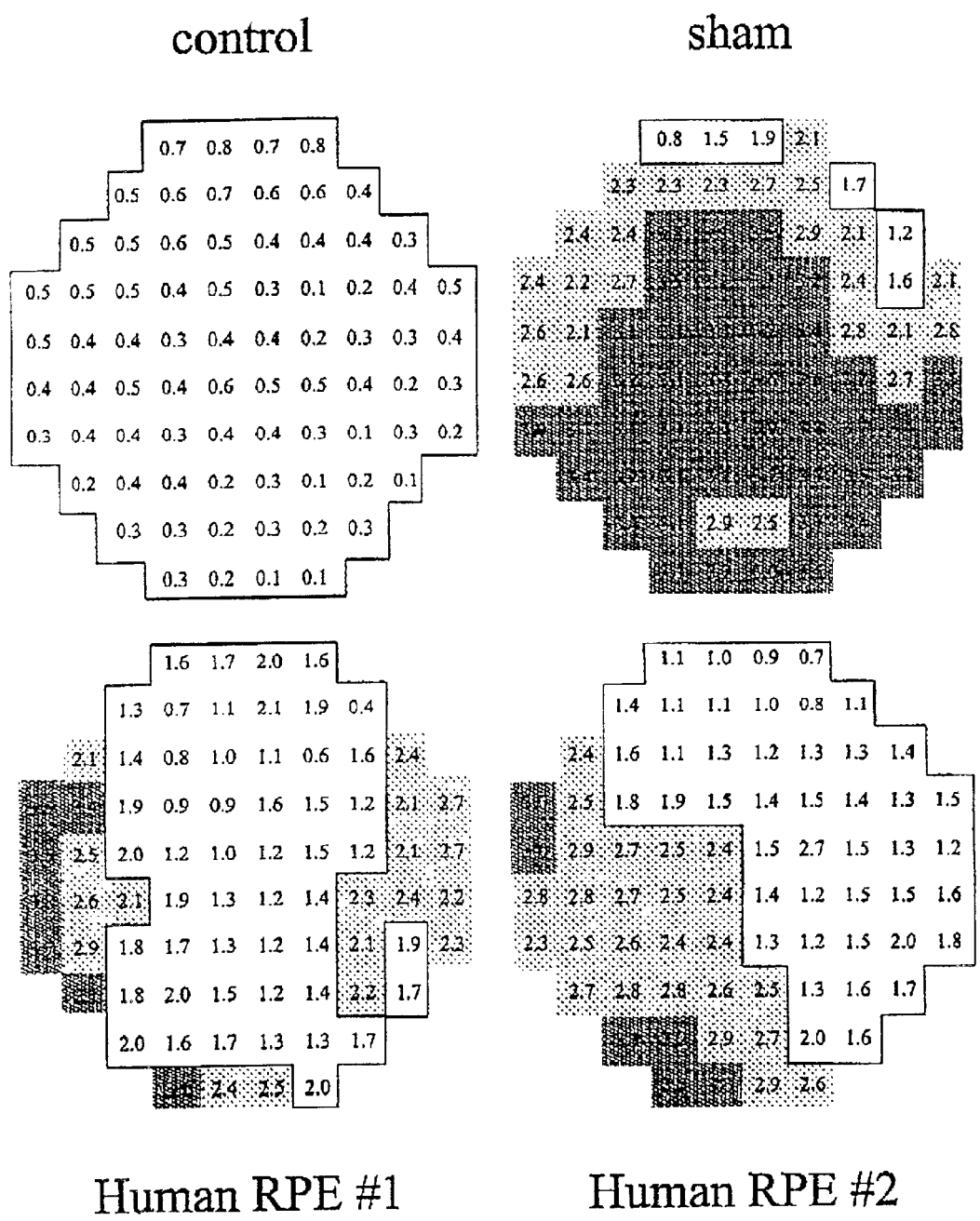

FIG. 24 is a set of recordings showing the threshold responses (details as in FIG. 22) recorded 12 weeks post-operative. Here the control was a non-dystrophic that received a graft. The sham injected animal shows evidence of remaining responsiveness seen in unoperated dystrophics around the edge of the superior colliculus. The 2 transplanted animals are examples showing substantially improved responsivenes.

FIGS. 25A–B are a set of photographs. FIG. 25A shows an aspect of the subcutaneous graft on cryostat section without any immunohistochemical treatment. The yellow/brown color is restricted to the graft zone (hRPE clone 7, 3 weeks post-implantation. Bright field, ×80). FIG. 25B shows a field of the same section at high magnification. The coloration is intracytoplasmic and present in the majority of the cells (Bright field, ×320).

FIGS. 26A–B are a set of photographs. FIG. 26A is a hematoxylin and eosin stain of hRPE clone 7, 3 weeks following subcutaneous post-implantation in the flank of a nude mouse (Bright field, ×40). FIG. 26B is a hematoxylin and eosin stain at high magnification of the same section. The colored cells show a normal structure of the nucleus. The graft is infiltrated by cells bearing elongated nuclei, probably fibroblasts (Bright field, ×800).

FIGS. 27A–B are a set of photographs showing Schmorl staining. FIG. 27A is a Schmorl stain of hRPE clone 7, 3 weeks following subcutaneous post-implantation in the flank of a nude mouse. The reaction with lipofuscins and/or melanin produce a blue/green staining of the cells within the graft site (Bright field, ×160). FIG. 27B is a Schmorl stain of hRPE clone 7, 15 weeks following subcutaneous implantation. A few green/black cells are found at the graft site (Bright field, ×160).

FIGS. 28A–F are an analysis of primary human RPE cells and human RPE cells with extended life-span. FIG. 28A and FIG. 28B are a set of phase contrast micrographs of (FIG. 28A) contact-inhibited monolayer of primary cultured human donor RPE cells 10 days after seeding and (FIG. 28B) of human clone hRPE7 cells derived from culture depicted in A (scale bars=100 μm). Both cultures exhibit cobblestone morphology characteristic of RPE cells. FIG. 28C shows the immunocytochemical detection by epifluorescence microscopy of SV40 large T antigen showing correct nuclear expression (scale bar=20 μm). FIG. 28D shows the immunocytochemical detection by confocal scanning laser microscopy (projected images) of junctional protein ZO-1 showing an almost continuous pattern of peripheral staining (scale bar=20 pin). FIG. 28E shows the immunocytochemical detection of the RPE cytokeratins 8 and 18. FIG. 28F is an overlay of images depicted in immunomicrographs D and E plus an additional bisbenzimide DNA stain (blue) to highlight the cell nuclei (scale bar 20 μm).

FIGS. 29 A–C are representation of head tracking to high contrast square-wave gratings. FIG. 29A is a photograph of head tracking apparatus showing RCS rat in holding chamber and rotating drum lined with square-wave grating. FIG. 29B shows the total amount of time spent tracking a moving square-wave grating in seconds over a period of 4 minutes after 10 weeks post-transplant. (FIG. 29C) Head tracking 20 weeks post-transplantation. Error bars represent s.e.m. *$p<0.01$ represents a significant difference as compared to both Sham and Dystrophic groups. +$p<0.05$ represents a significant difference as compared to the hRPE7 group.

FIGS. 30A–E are a set of recordings showing the threshold light sensitivity maps of congenic, dystrophic, hRPE7 transplanted and sham operated ROS rats. RCS rats were divided into 4 groups: (FIG. 30A) normal (3 non-dystrophic rats); (FIG. 30B) no treatment (6 dystrophic rats); (FIG. 30C) hRPE7 cells injected into one eye (5 dystrophic rats); and (FIG. 30D) sham injected (5 dystrophic rats). Schematic representation of a dorsal view of the superior colliculus showing respective thresholds for 76 individual recording sites (color coded squares). A log scale of thresholds measured in candela/$m^2$ is shown. To test efficacy of hRPE7 grafts versus sham injected animals, significance was determined at each of the 76 points using a randomization test. An area of significantly improved visual function was recorded for the hRPE7 transplanted animals as shown in (FIG. 30E). The corresponding topological representation of the retina onto the superior colliculus is indicated by the letters D (dorsal), V (ventral), N (nasal), and T (temporal). The arrow represents the grafted quadrant.

FIGS. 31A–C are a set of photographs showing anatomical changes in the photoreceptor cell layer following transplantation of hRPE7 in RCS rats. Sections of the retina from (FIG. 31A) a 6-month-old non-dystrophic RCS rat showing full outer nuclear layer thickness. (FIG. 31B) Sham operated RCS rat 5 months post operation showing complete ablation of the outer nuclear layer. (FIG. 31C) hRPE7 transplanted RCS rat 5 months post graft demonstrating significant preservation of the outer nuclear layer. Sections were stained with cresyl violet. GC: ganglion cell layer. INL: inner nuclear layer. ONL: outer nuclear layer. RPE: retinal pigment epithelial cell layer. Scale bar=25 μm. Panel (FIG. 31A) is also stained with RT-97 anti-heavy neurofilament antibody.

FIGS. 32A–B are a set of bar graphs showing an assessment of visual function in RCS with the hRPE cell line 7 (passages 14 and 21) as compared to those with hRPE-19. The results are obtained from a visual stimulus, which moves in an anti-clockwise direction, which viewed from the right eye is a temporal to nasal direction. All transplants were placed in the superior temporal retina of the right eye. Data represent the total time spent head tracking. Experimental groups: Con: non-dystrophic RCS rats (n=10), Dys: un-treated dystrophic RCS rats (n=10), Sham: dystrophic RCS rats received injection of 1 μl cell culture medium (used for hREP7; n=8). H1RPE7p14: hRPE7 at passage 14 injected into dystrophic RCS rats (n=10), H1RPE7p21: hRPE7 at passage 21 injected into dystrophic RCS rats (n=7), ARPE-19p22: ARPE-19 at passage 22 injected into dystrophic RCS rats (n=5). FIG. 32A shows, for comparison, data of each experimental group were pooled over all square wave gratings (0.125, 0.25 and 0.5 cycles/degree). A significant difference ($p<0.01$) is apparent between the groups which either received cell grafts or remained untreated (sham, dystrophics). ARPE-19 clearly shows a therapeutic effect which comes close to hRPE7p21. FIG. 32B shows the total time spent head tracking at 0.125 cycles/° and 0.25cycles/° grating stimulus. While congenic animals were also able to track a grating of 0.5 cycles/degree none of the other groups (including transplanted groups) were able to do so.

DETAILED DESCRIPTION OF THE INVENTION

In one advantageous embodiment of the lines, cell lines are derived from retinal endothelial cells and exhibit the morphological characteristics and antigen expression characteristics of the primary culture retinal endothelial cells, namely fusiform morphology, expression of the endothelial tissue markers (such as RPCA-1), the constitutive expression of markers specific for the CNS endothelium (such as P-glycoprotein, GLUT-1, and the transferrin receptor), and the absence of expression of surface antigens specific for the cerebral endothelial cells (such as the 1A8B antigen).

In another advantageous embodiment of the lines, cell lines are derived from retinal pigment epithelial (RPE) cells and exhibit the morphological characteristics and antigen expression characteristics of the primary culture retinal pigment epithelial cells (namely pavement morphology and expression of RET-PE2 and cytokeratins).

Surprisingly, the cells of such cell lines do not differ in their expression of the characteristics of the differentiated retinal endothelial cells or the differentiated retinal pigment epithelial cells. Moreover, the retinal pigment epithelial cells are capable, in vivo, of integrating appropriately into the cytoarchitecture of the retina of a host mammal without proliferating, and of preventing the loss of photoreceptors, especially in rats of the Royal College of Surgeons (RCS) strain (see, EXAMPLES 10 and 11). The retinal endothelial cells are also capable, in vitro, of serving as a model for the blood-retina barrier in the absence or presence of the retinal pigment epithelial cells.

In another advantageous embodiment of the cell lines, the polynucleotide containing an oncogene contains a heat-sensitive SV40 T-oncogene. This gave retinal endothelial cells with extended life-span, such as IO/JG2/1, which were fusiform like the primary culture cells and expressed the above-mentioned markers specific for the CNS endothelial cells, as well as the same surface antigens and the same antigens of the major histocompatibility complex as the primary culture retinal endothelial cells. This also gave retinal pigment epithelial (RPE) cells with extended life-span, such as IO/LD7/4 or hRPE (FIGS. 23–32), which were very similar to the primary culture cells, although not pigmented. These cells express the specific RET-PE2 antigen and the cytokeratins.

The lines of the invention (cell lines and vector lines) have the advantage of constituting a pure, homogeneous, and sufficient source of cells of retinal origin for the purpose of reproducible application to transplantations, especially because all these lines have the phenotype of the primary culture lines.

The vector lines integrate well into the retinal vascularization, are very well tolerated, release in vivo over a long period the active substance which they express, and can be used in the preparation of a composition for the treatment of primary or secondary ophthalmologic or neurological disorders.

The retinal endothelial cells with extended life-span called IO/JG2/1 were deposited under no. I-1695 on 18, Apr. 1996 in the Collection Nationale de Cultures de Micro-organismes (CNCM) held by the Institut Pasteur, 28 rue de Docteur Roux, 75724 PARIS CEDEX 15, FRANCE.

The retinal pigment epithelial cells with extended life-span called IO/LD7/4 were deposited under no. I-1694 on 18, Apr. 1996 in the Collection Nationale de Cultures de Micro-organismes (CNCM) held by the Institut Pasteur.

The subject cultures are deposited under conditions that ensure that access to the cultures will be available during the pendency of the patent application disclosing them to one determined by the Commissioner of Patents and Trademarks to be entitled thereto under 37 C.F.R. § 1.14 and 35 U.S.C. § 122. The deposits are available as required by foreign patent laws in countries where counterparts of the subject application, or its progeny, are filed. However, the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least 30 years after the date of deposit or for the enforceable life of any patent which may issue disclosing the cultures plus 5 years after the last request for a sample from the deposit. The depositor acknowledges the duty to replace the deposits should the depository be unable to furnish a sample when requested, due to the conditions of the deposits. All restrictions on availability to the public of the subject culture deposits will be irrevocably removed upon granting of a patent disclosing them.

In an advantageous embodiment of the cell lines, the polynucleotide that extends life-span is selected in the group consisting of viral oncogenes such as SV-40 large T oncogene, the EIA early region of the adenovirus 2 genome or cellular oncogenes such as c-myc and Ha-ras, or human telomerase reverse transcriptase gene (hTRT), or a sequence that activates the hTRT endogenous gene.

In another advantageous embodiment of the cell lines, the cell lines further comprise an expression vector comprising a sequence coding for a polypeptide or a protein or they may further produce a viral vector. The expression vector may be carried by a plasmid or a viral vector. The viral vectors may advantageously be selected in the group consisting of LTR-based MFG, LXSN, LNSX and LNCX (Byun et. al., 3 Gene Therapy 780–788 (1996); Kim et al., 72J. Virol. 994–1004 (1998)).

In an advantageous embodiment of the method, the cell lines further comprise an expression vector comprising a sequence coding for a polypeptide, a protein or a viral vector, as defined above. According to the method, the step of grafting the retinal pigment epithelial cells comprises a surgical injection of the cells into the subretinal space of a subject (such as a patient).

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

Apart from the foregoing provisions, the invention also comprises other provisions, which will become apparent from the following description referring to EXAMPLES of how to carry out the process forming the subject of the present invention, and to the attached drawings. The following EXAMPLES are presented in order to more fully illustrate the preferred embodiments of the invention. It must be clearly understood, however, that these EXAMPLES are given solely in order to illustrate the subject of the invention, without in any, way implying a limitation.

EXAMPLE 1

Methods Used to Characterize the Cells of the Invention (a) Isolation and culture of rat aortic endothelial cells. The aortic endothelium was isolated by the method described by McGuire et al., 57 Lab. Invest. 94–105 (1987). The rat aorta was removed by dissection and cut into small pieces (2–5 mm), which were placed on 24-well plates coated with collagen and containing an endothelial cell culture medium, in such a way that the luminal face of the pieces of aorta was in contact with the collagen. The RPMI culture medium was supplemented with 20% fetal calf serum, 7.5 $\mu$g/ml endothelial cell growth supplement, 80 $\mu$g/ml heparin, 2 mM glutamine, 0.5 $\mu$g/ml vitamin C, 100 U/ml penicillin, and 100 $\mu$g/ml streptomycin.

After 3 days, the explants were removed and the adhering cells were proliferated to the point of confluence. At confluence, the cells had a pavement morphology characteristic of the endothelial vessels, expressed Von Willebrand's factor, and proliferated in a medium containing D-valine. The cells were used after 3 passages (earliest stage for experimental use).

(b) Protocol for carrying out electron microscopy for the morphological assay of the different cells obtained. The monolayers of the cells with extended life-span (retinal endothelial cells and retinal pigment epithelial cells) were cultivated in 24-well plates to the point of confluence. The cells were fixed with a mixture of 1% paraformaldehyde and 3% glutaraldehyde in 0.1 M sodium cacodylate HCl (pH 7.4), or 2.5% glutaraldehyde in 0.1 M sodium cacodylate buffered to pH 6.9 by the addition of 0.5% (w/v) tannic acid.

After being rinsed 3 times (3×) for 5 minutes (min) in a sodium cacodylate buffer (pH 7.4), the cells were fixed again for 2 hours (hr) at 4° C., in the absence of light, in 1% aqueous osmium tetroxide solution, dehydrated in the presence of different strengths of alcohol (1×10 mm 50–90%, 4×10 mm 100%), included in Araldite, and cured at 60° C. for 12 hr. Semi-thin (1 μm) and ultra-thin (50 nm) sections were prepared using a Leica Ultracut S® microtome. The semi-thin sections were stained with 1% toluidine blue in 50% ethanol for microscopic observation. The ultra-thin sections were stained sequentially with 1% lead citrate in 50% ethanol and with lead citrate and were observed and photographed with a JEOL 1010 transmission electron microscope operating at 80 kV.

(c) Protocol for detecting the endothelial and epithelial surface antigens by ELISA, immunohistochemistry, and flux cytometry.

(1) ELISA. Rat retinal endothelial cells (primary culture and cells with extended life-span) were inoculated at confluence density onto 96-well plates which had first been coated with 0.05% type IV collagen. Before the cells were plated, the collagen was fixed in ammonia vapor and the plates were washed twice with Hanks' buffered saline solution (HBSS). The cells were cultivated for 3 days before experimental use. After the experimental treatments, the cells were washed 4× in Hanks' buffered saline solution and fixed with 0.1% glutaraldehyde in phosphate-buffered saline (PBS) for 10 min at room temperature. The cells were washed with 50 mM Tris-HCl buffer, pH 7.5, for 20 min at room temperature. The primary antibodies were diluted in 100 μl of Hanks' buffered saline solution containing 100 μ/ml of normal rabbit IgG and 4 mg/ml of bovine serum albumin and then incubated with the cells for 45 min at 37° C. The cells were washed 4× with phosphate-buffered saline containing 0.2% Tween 20 and then incubated with a biotinylated anti-mouse IgG (1:700; Amersham) for 45 min at 37° C. The cells were washed again 4× with phosphate-buffered saline containing 0.2% Tween 20 and incubated with horseradish peroxidase/streptavidin (1:700; Amersham) for 45 min at 37° C. The cells were washed 4× in phosphate-buffered saline containing 0.2% Tween 20 and incubated with 100 μl of tetramethylbenzidine in a citrate-acetate buffer (pH 5) for 10 min. The reactions were stopped by the addition of 50 μl of 1 M sulfuric acid and the reaction product was quantified (optical density at 450 nm).

(2) Histochemical studies. The primary cultures and cells with extended life-span were inoculated onto slides (Gibco/BRL) and cultivated to the point of confluence. The surface antigens were detected by washing the cells in Hanks' buffered saline solution and then blocking with Hanks' buffered saline solution containing 100 μ/ml of normal rabbit IgG and 4 mg/ml of bovine serum albumin. The primary antibodies were then added to the non-fixed cells, the cells were incubated for 1 hr on ice and washed. A second, antibody-specific biotinylated antibody was added and the cells were incubated for 30 min. After a washing, FITC-labeled streptavidine was incubated with the cells for 15 min. The cells were then fixed, mounted and observed under a Zeiss Axiophot®. For the intracellular antigens, the cells were fixed and rendered permeable as described above for the ELISA method.

(3) Flux cytometry. The flux cytometry of the confluent retinal cultures was carried out on a FACScan apparatus (Becton-Dickinson). After washing, the cellular monolayers were dissociated in Hanks' buffered saline solution containing 1 mg/ml of collagenase/dispase and 0.2% EDTA and the cells were resuspended in phosphate-buffered saline. $5 \times 10^4$ cells/flask were incubated for 1 hr with the primary antibody on ice, this being followed by a second incubation for 1 hr with an anti-mouse IgG rabbit F(ab')$_2$ antibody conjugated with HTC, in the presence of 20% normal rat serum. After 2 washes, the cells were resuspended in phosphate-buffered saline and analyzed. The non-stained cells were used for calibration and the cells stained only with the second antibody were used to establish the background.

(d) Protocol for assaying the migration of the T-lymphocytes across the monolayer. The capacity of the cells with extended life-span to allow the trans-endothelial migration of the T-cells specific for the antigen was determined as described in Greenwood et al., 80 Immunol. 401–6 (1993). The T-cells ($2 \times 10^5$ cells/ml/well) were introduced into 24-well plates containing monolayers of primary cell culture or retinal endothelial cells with extended life-span and retinal pigment epithelial cells with extended life-span. The T-cells sediment and migrate in 4 hr. To evaluate the migration rate, the co-cultures were placed under a phase contrast microscope and maintained at 37° C. and in an atmosphere containing 5% $CO_2$. A 200×200 μm field was chosen at random and recorded for 10 min, spread out over a 4 hr period, with a camera. The data were expressed as the percentage of total lymphocytes in a field that had migrated across the monolayer; a minimum of 6 wells/test were analyzed.

EXAMPLE 2

Preparation of a Line According to the Invention

Rat Retinal Endothelial Cells (a) Isolation and culture of the retinal endothelial cells. Endothelial cells were derived from 4- to 6-week-old female Lewis rats free of pathogens. The retinal cells were isolated and cultivated by the methods described by Greenwood, 39 J. Neuroimmunol. 123–132 (1992) and Abbott et al., 103 Cell Sci. 23–37 (1992). These techniques produced primary cultures with a purity in excess of 95%. The rat retinas were dispersed by enzymatic digestion, the fragments of microvessels were separated from the cells themselves by centrifugation and the cells were washed and cultured in flasks coated with collagen. The growth medium consisted of Ham's F-10 medium (Sigma, St. Louis, Mo.) supplemented with 17.5% serum (Advanced Protein Products Ltd.); 7.5 μg/ml of endothelial cell growth supplement (Advanced Protein Products Ltd.); 80 μg/ml of heparin, 2 mM glutamine; 0.5 μg/ml of vitamin C; 100 U/ml of penicillin; and 100 μg/ml of streptomycin.

The cultures were maintained at 37° C. in an atmosphere containing 5% $CO_2$. The medium was replaced every 3 days to the point of confluence.

(b) Transfection of the cells. A retroviral vector containing the SV40 T-gene, which is replication-deficient, was obtained according to the technique described by Jat et al., 6(4) Mol. Cell. Biol. 1204–17 (1986) The retroviral vector was produced in quantity in selected fibroblast lines (SVU19.5 line). This retroviral vector codes for a tsa58 T-antigen, which is temperature-sensitive and associated with the gene coding for neomycin as a selection marker. The vector was obtained from the culture supernatant of SVU 19.5 cells after passage through a 0.45 μm filter to remove the producer cells. The vector was added to a primary culture of endothelial cells such as those prepared in (a) (transfection). 200 μl of virus in 2 ml of a medium containing 8 μg/ml of Polybrene® (Aldrich) were added to the endothelial cells. The whole was incubated for 4 hr at 37° C. in an incubator under a 5% $CO_2$ atmosphere, the flask being shaken every 15 min.

IO/JG2/1), whereas no staining was observed in the endothelial cells of the primary cultures.

(4) Expression of endothelial markers. The IO/JG2/1 clone expressed a number of antigens specific for the endothelial cells. The results obtained were illustrated in TABLE 1.

TABLE 1

| Antigen | REC primary | | | IO/JG2/1 clone | | | CEC primary | | | Aortic EC | | |
|---|---|---|---|---|---|---|---|---|---|---|---|---|
| | Base level | IFN | TNF | Base level | IFN | TNF | Base level | IFN | TNF | Base level | IFN | TNF |
| P-glycoprotein (JSB-1) | + | nd | nd | + | nd | nd | + | nd | nd | − | nd | nd |
| GLUT-1 | + | nd | nd | + | nd | nd | + | nd | nd | − | nd | nd |
| Von Willebrand's factor | + | nd | nd | + | nd | nd | + | nd | nd | + | nd | nd |
| Transferrin receptor (OX-26) | + | nd | nd | (+) | nd | nd | + | nd | nd | − | nd | nd |
| RECA-1 | + | nd | nd | + | nd | nd | + | nd | nd | nd | nd | nd |
| ICAM (3H8/1A-29) | + | + | + | + | + | + | + | + | + | + | + | + |
| VCAM-1 (5F10) | − | + | − | − | + | + | − | + | + | + | + | + |
| PECAM-1 | + | nd | nd | + | nd | nd | + | nd | nd | + | nd | nd |
| Non-EC CNS (OX-43) | − | nd | nd | − | nd | nd | − | nd | nd | − | nd | nd |
| CD44 (OC-50) | + | nd | nd | + | nd | nd | + | nd | nd | + | nd | nd |
| Class I MHC (OC-18) | + | + | + | + | + | + | + | + | + | + | + | + |
| Class III-A MHC (OC-6) | − | (+) | − | − | + | − | − | + | − | − | + | − |
| 3H12B | + | + | + | (+) | + | + | + | + | + | + | + | + |
| 4A2 | + | + | + | + | + | + | + | + | + | + | + | + |

EC CNS = Endothelial cells of the central nervous system
REC primary = retinal endothelial cells in primary culture
CEC primary = cerebral endothelial cells in primary culture After incubation, the medium was removed and 5 ml of fresh medium were added; the whole was recultivated overnight. The cells were then kept in the incubator for 48 hr. The cells were then plated on a selective medium containing 200 μg/ml of geneticin (G418, Gibco) and the parental lines were obtained by selection of the resistant colonies. Cloning by limiting dilution of the parental line gives particularly the selected IO/JG2/1 clone for a more thorough analysis.

(c) Characteristics of the IO/JG2/1 clone. The IO/JG2/1 clone was cultivated up to the $30^{th}$ passage without significant morphological or phenotypic differences.

Figure 1B:
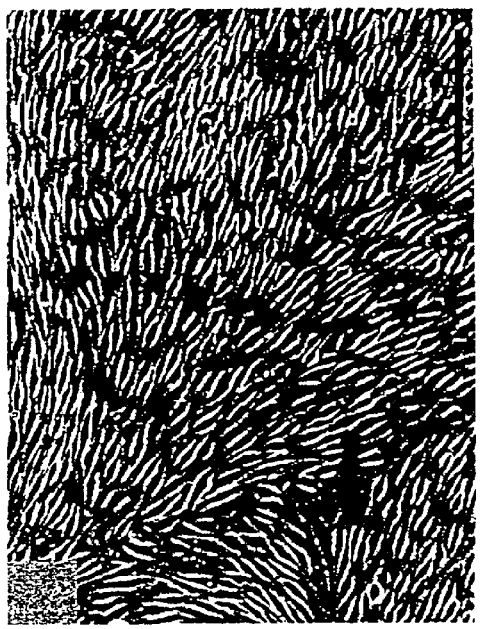
FIG. 1B is a photomicrograph showing the morphology of the primary cultures of retinal pigment epithelial cells.
Figure 1D:
FIG. 1D is a photomicrograph showing the morphology of the primary cultures of IO/LD7/4 clones.
Figure 1A:
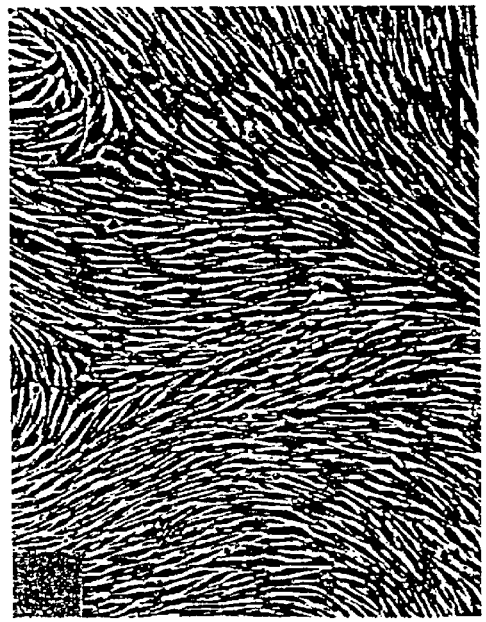
FIG. 1A is a photomicrograph showing the morphology of the primary cultures of retinal endothelial cells.

(1) Morphology. The primary cultures of retinal endothelial cells had a fusiform morphology characteristic of these cells (FIG. 1A). The IO/JG2/1 clone conserved this characteristic morphology (FIG. 1B).

(2) Ultrastructural appearance. The ultrastructural appearance of the IO/JG2/1 clone (FIG. 2B, FIG. 2C) was similar to that of the primary cultures. A voluminous nucleus was observed together with the presence of peripheral heterochromatin and numerous cytosolic organelles such as mitochondria, endoplasmic reticulum and polysomes. The junctions between the cells often exhibit interdigitation with regions of cytoplasmic density at the narrow points of contact. The cells rest on a lamina basalis.

Figure 3A:
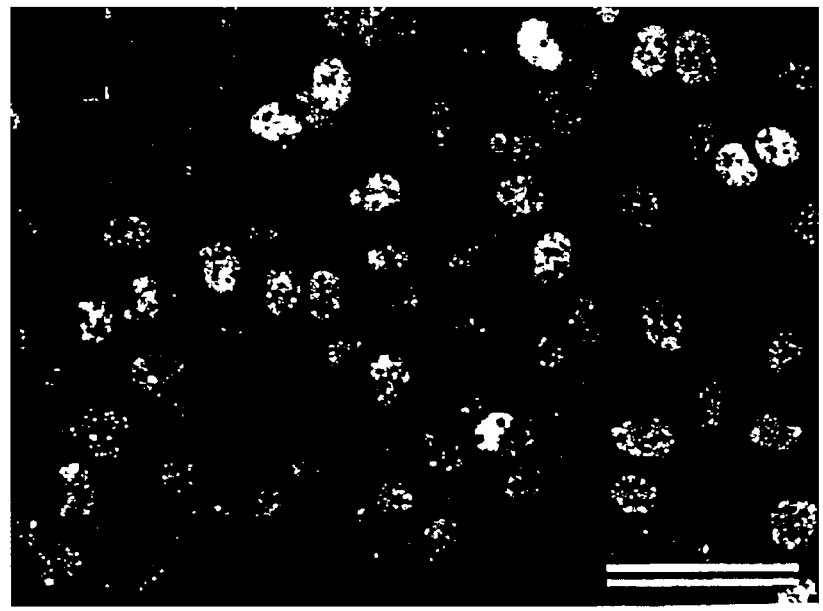
FIG. 3A is a micrograph showing the nuclear staining obtained in the presence of antibodies directed against the T-antigen in IO/JG2/1 cells.

(3) Expression of the tsa58 T-antigen. All the retinal endothelial cells with extended life-span selected in the G418 medium showed substantial nuclear staining with antibodies directed against the T-antigen (FIG. 3A;

TABLE 1 shows that the IO/JG2/1 clone expressed Von Willebrand's factor, the REC-1 antigen, the ICAM-1 antigen (the expression of which can also be induced by treatment with 100 U/ml of IFNγ or TNFα for 24 hr (TABLE 1; FIG. 4; and FIG. 6)), and the VCAM-1 antigen, after induction by the above-mentioned cytokines (200 U/ml of IFN γ or TNFα for 24 hr or 48 hr) (cf. TABLE 1).

(5) Expression of endothelial markers specific for the CNS. TABLE 1 also shows that the IO/JG2/1 clone constitutively expressed a number of markers specific for the endothelial cells of the CNS, especially P-glycoprotein, GLUT-1 and the transferrin receptor (cf. TABLE 1). However, the IO/JG2/1 clone did not express some of the antigens specific for the cerebral endothelial cells, especially the 1A8B and 2A4 antigens. This characteristic makes it possible to differentiate the IO/JG2/1 clone from the cerebral endothelium (TABLE 2 below).

(6) Comparison of the expression of the endothelial antigens in the primary cultures and the lines with the peripheral endothelial cells. As described above, the primary cultures of retinal endothelium and the derived clones expressing the T-antigen showed a constitutive expression of the markers specific for the endothelial cells of the CNS, namely P-glycoprotein, GLUT-1 and the transferrin receptor (TABLE 2), whereas the aortic endothelium does not express these antigens but does express the OX-43 antigen, which is considered to be specific for the peripheral endothelial cells. The OX-43 antigen was effectively not expressed either by the primary cultures or by the cultures of cerebral cells with extended life-span and the cultures of retinal endothelial cells with extended life-span (TABLE 1).

These different cultures were also screened against a sample group of antigens considered to be specific for the cerebral endothelial cells: The results were illustrated in TABLE 2.

TABLE 2

| Antigen | REC primary | IO/JG2/1 clone | CEC primary | Aortic EC |
|---|---|---|---|---|
| 3B7 | + | | | + |
| 3D11 | + | + | + | + |
| 3D7B | + | (+) | + | + |
| 4C6C | | (+) | + | + |
| 2F1B | + | + | + | + |
| 2A4 | | | + | + |
| 4E3 | + | + | + | + |
| 2A5 | + | + | + | + |
| 1A8B | | | + | + |
| 1C1 | + | | + | + |
| 1C11 | + | + | + | + |
| 1D2 | + | | + | + |
| 4E8.C4 | + | + | + | + |

(7) Expression of the antigens of the major histocompatibility complex. All the endothelial cultures showed a constitutive expression of the class I major histocompatibility antigens (OX-18, cf. TABLE 1 and FIGS. 4, 6 and 7), which was induced by 100 U/ml of rat recombinant IFNγ for 24 hr. The primary cultures of retinal and cerebral endothelial cells, and the parental lines and the clones expressing the T-antigen, showed very little or no expression of the class II major histocompatibility antigens. Cultures of endothelial cells treated for 24 hr only with 100 U/ml of recombinant IFNγ exhibit a substantial induction of certain class II antigens: OX-6 and OX-17 (cf Table I and FIG. 4).

Figure 8:
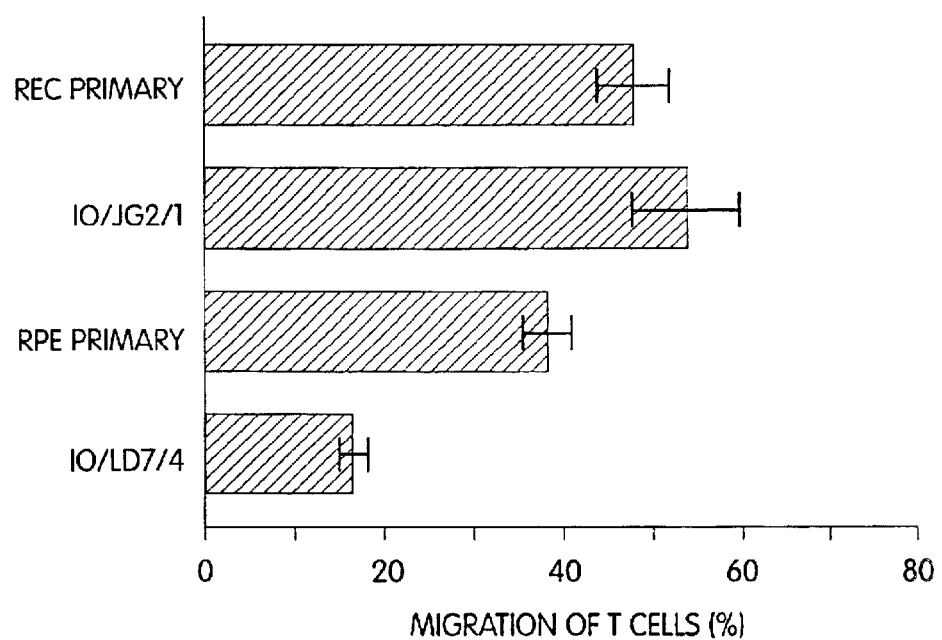
FIG. 8 is a bar graph showing the migration of T-lymphocytes across monolayers consisting of the primary cultures of retinal endothelial cells (REC), retinal pigment epithelial cells (RPE) or the IO/JG2/1 and IO/LD7/4 clones.

(8) Migration of the T-lymphocytes across the monolayer. No significant difference existed between the capacity of the primary cells and that of the cells with extended life-span to support specific T migration. The degree of migration across the monolayers in the course of a 4 hr test was 52±5% for the cerebral primary endothelial cells, 48±4% for the retinal primary endothelial cells and 54±6% for the IO/JG2/1 retinal endothelial clone (FIG. 8).

EXAMPLE 3

Preparation of a Line According to the Invention

Rat Retinal Epithelial Cells (a) Isolation and culture of the retinal pigment epithelial cells. The rat retinal pigment epithelial cells were isolated from 6-day to 8-day old PVG rats according to the method of Chang et al., 10 Curr. Eye Res. 1081–1086 (1991). The eyes were removed and the intact eyeballs were digested with 2% dispase for 30 min. The eyes were then dissected for removal of the cornea and the vitreous body. The dissected retina was then isolated and incubated for 15 min in a culture medium. After incubation, layers of retinal pigment epithelial cells were separated from the neuroretina and treated with trypsin to produce a cellular suspension. The cells were plated in tissue culture flasks and cultivated to the point of semiconfluence. The culture medium consisted of Ham's F-10 medium supplemented with 20% fetal calf serum, 20 mM HEPES, 7.5% sodium bicarbonate, 2 mM glutamine, 100 U/ml of penicillin and 100 μg/ml of streptomycin. These primary cultures grew in the form of pigmented monolayers, which were positive for the cytokeratins and the epitope specific for the retinal pigment epithelial, namely RET-PE2 (Nell et al., 51 Exp. Eye Res. 573–583 (1990).

(b) Transfection of the cells. These cells were prepared under the same conditions as those described in EXAMPLE 2, with the exception of the incubation time with the retroviral vector, which was 2 hr. The parental lines were obtained by selection of the resistant colonies. Cloning by limiting dilution of the parental line gave the IO/LD7/4 clone, which was selected for a more thorough analysis.

(c) Characteristics of the IO/LD7/4 clone. The IO/LD7/4 clone was cultivated up to the $52^{nd}$ passage with no significant phenotypic differences.

Figure 1C:
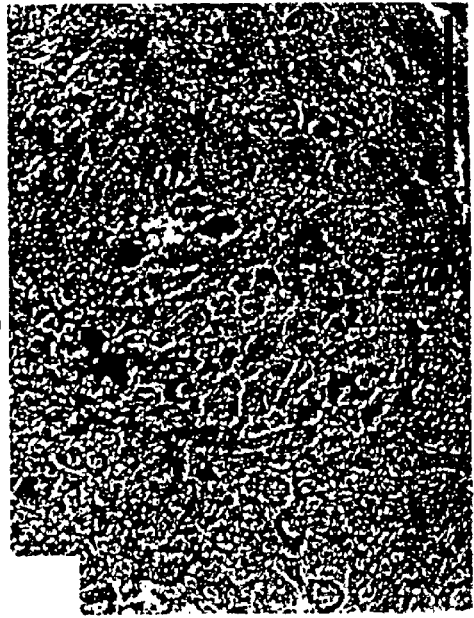
FIG. 1C is a photomicrograph showing the morphology of the primary cultures of the IO/JG2/1 clones.
Figure 2A:
FIG. 2A is a transmission electron micrographs of the IO/LD7/4 cells.
Figure 2B:
FIG. 2B is a transmission electron micrographs of the IO/JG2/1 cells.
Figure 2C:
FIG. 2C is a transmission electron micrographs of the IO/JG2/1 cells.

(1) Morphology. The morphology of the retinal pigment epithelial cells with extended life-span (FIG. 1D) was similar to that of the primary cultures (FIG. 1C). In contrast to the primary cultures, the cells with extended life-span were not pigmented. p1 (2) Ultrastructural appearance. Although the cells of the IO/LD7/4 clone were not pigmented when observed under the microscope, the TEM reveals dense bodies with the appearance of premelanosomes (FIG. 2A).

Figure 3B:
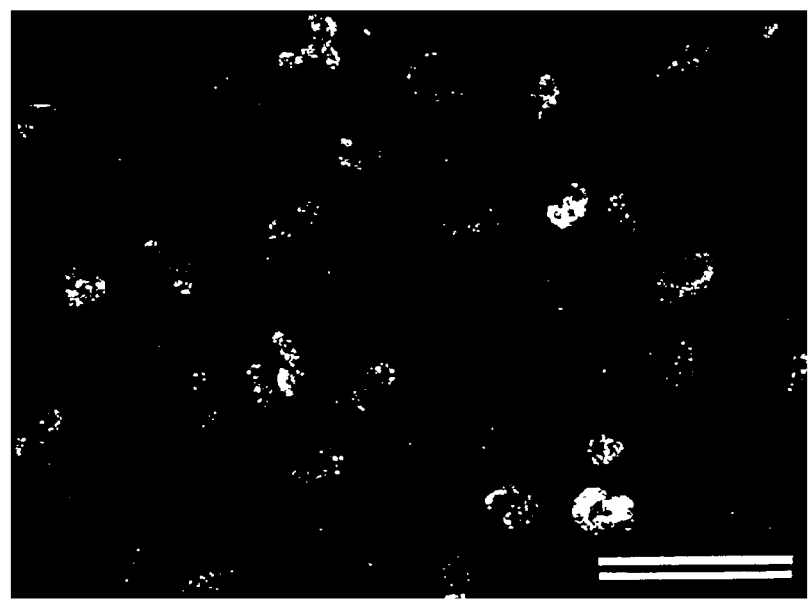
FIG. 3B is a micrograph showing the nuclear staining obtained in the presence of antibodies directed against the T-antigen in IO/LD7/4 cells
Figure 4A:
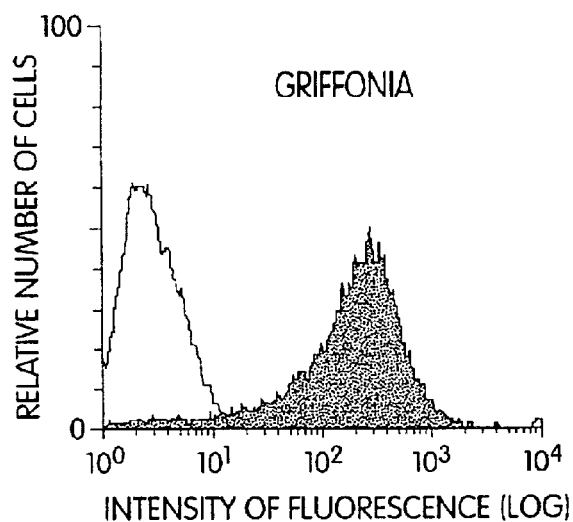
FIG. 4A is a graph showing the expression of endothelial marker, Griffonia in the IO/JG2/1 cultures.
Figure 4B:
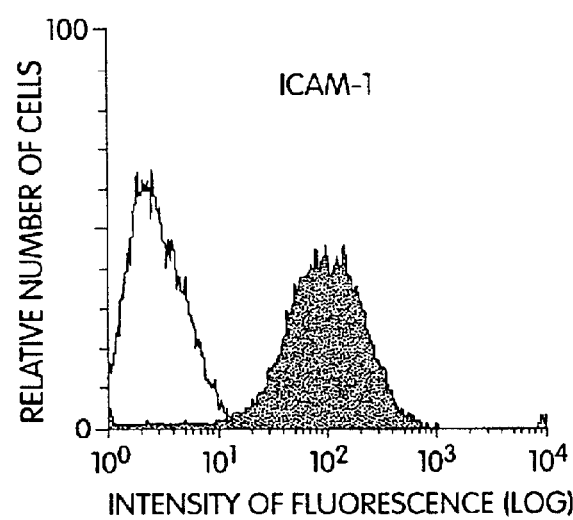
FIG. 4B is a graph showing the expression of endothelial marker, ICAM-1 in the IQ/JG2/1 cultures.
Figure 4C:
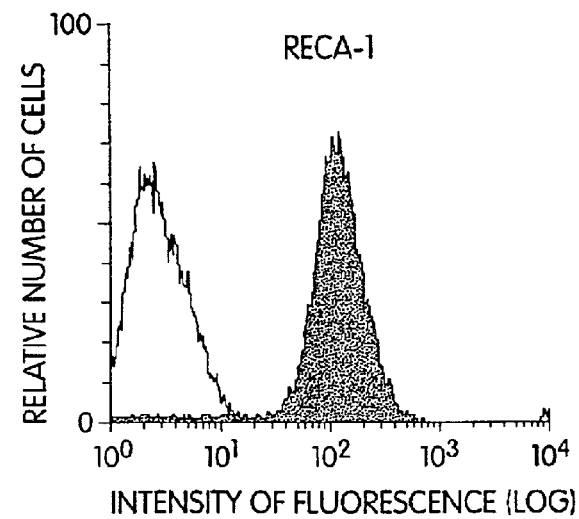
FIG. 4C is a graph showing the expression of endothelial marker, RECA-1 in the IO/JG2/1 cultures.
Figure 4D:
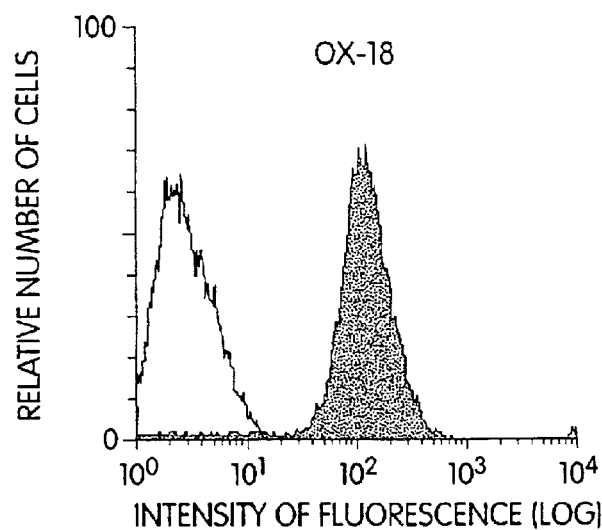
FIG. 4D is a graph showing the expression of endothelial marker, OX-18 in the IO/JG2/1 cultures.
Figure 4E:
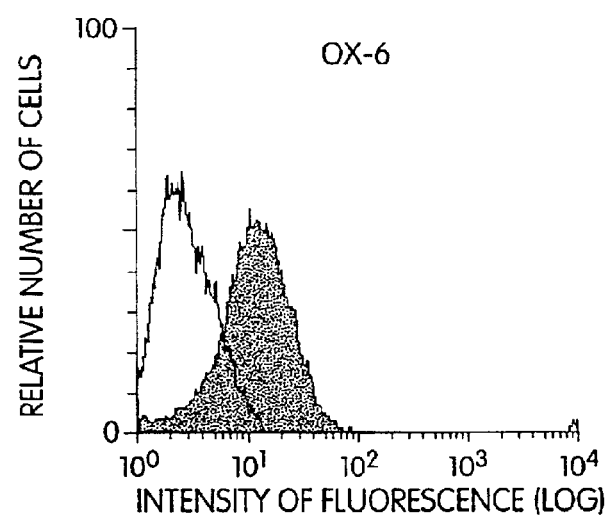
FIG. 4E is a graph showing the expression of endothelial marker, QX-6 in the IO/JG2/1 cultures.
Figure 4F:
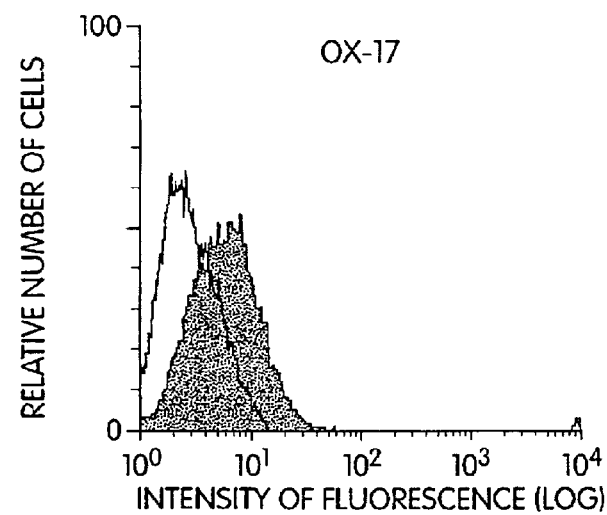
FIG. 4F is a graph showing the expression of endothelial marker, OX-17 in the IO/JG2/1 cultures.
Figure 5A:
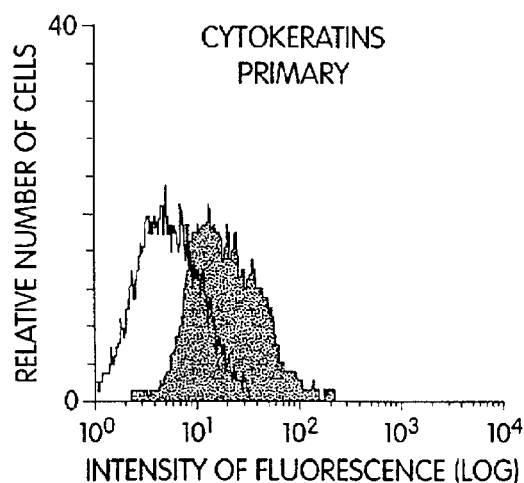
FIG. 5A a graphs showing the comparative expression of epithelial marker, cytokeratin in the primary cultures.
Figure 5B:
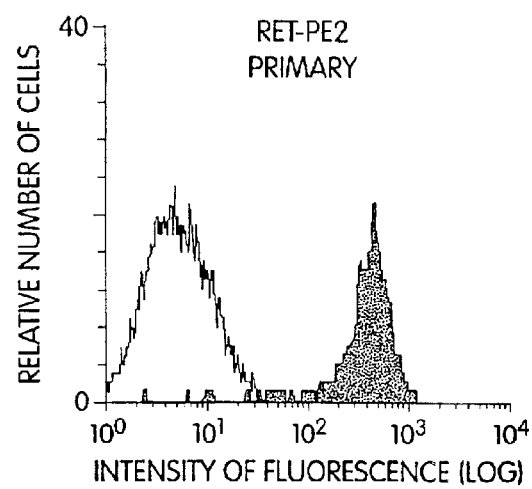
FIG. 5B a graphs showing the comparative expression of epithelial marker, RET-PE2 in the primary cultures.
Figure 5C:
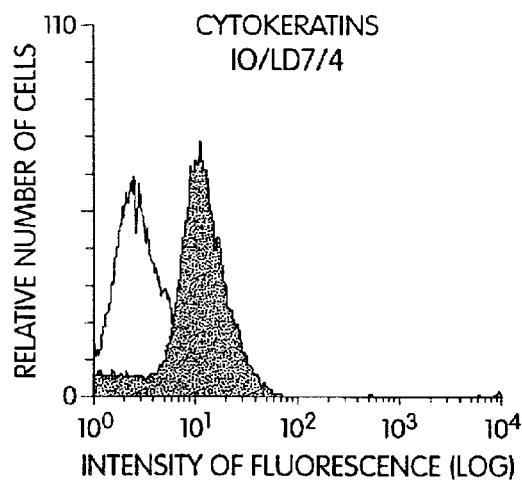
FIG. 5C a graphs showing the comparative expression of epithelial marker, cytokeratin in the IQ/LD7/4 clone.
Figure 5D:
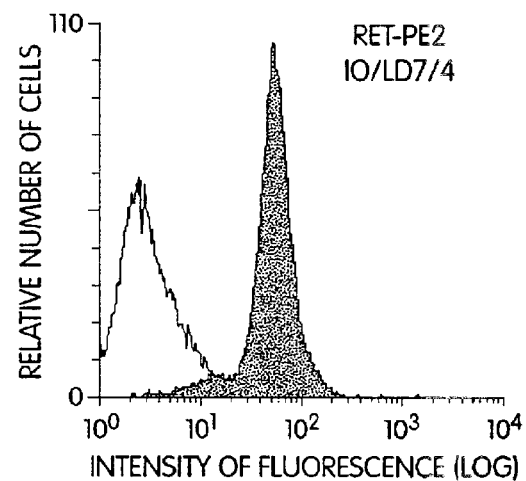
FIG. 5D a graphs showing the comparative expression of epithelial marker, RET-PE2 in the IO/LD7/4 clone.
Figure 6A:
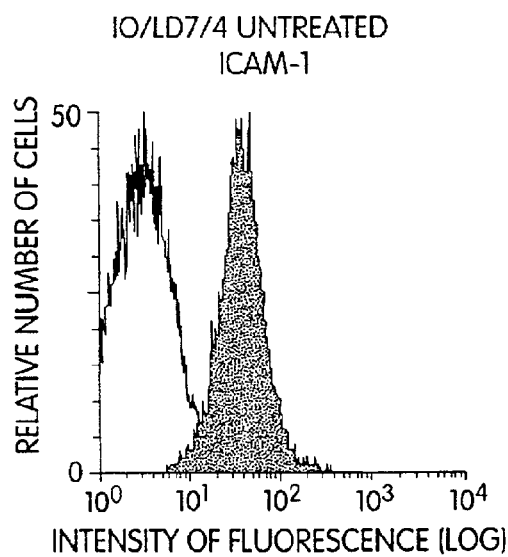
FIG. 6A is a graph showing the expression of the adhesion molecule ICAM-1 in the IO/LD7/4 clone in the absence of induction by interferon gamma (IFNγ).
Figure 6B:
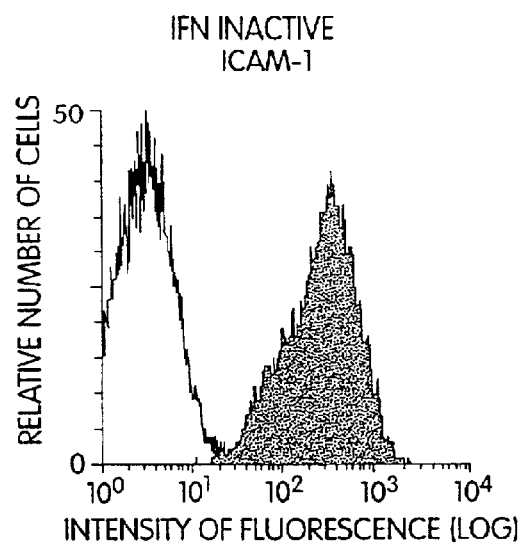
FIG. 6B is a graph showing the expression of the adhesion molecule ICAM-1 in the IO/LD7/4 clone in the presence of induction by interferon gamma (IFNγ).
Figure 6C:
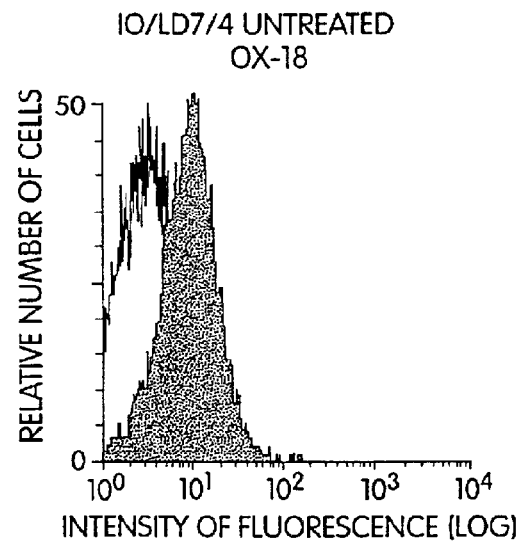
FIG. 6C is a graph showing the expression of the adhesion molecule OX-18 in the IO/LD7/4 clone in the absence of induction by interferon gamma (IFNγ).
Figure 6D:
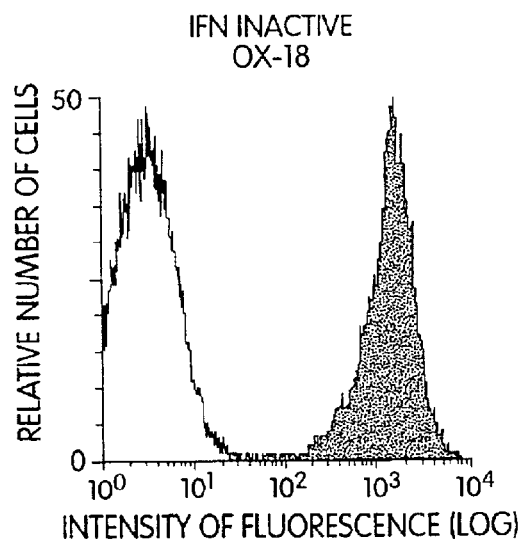
FIG. 6D is a graph showing the expression of the adhesion molecule OX-18 in the IO/LD7/4 clone in the presence of induction by interferon gamma (IFNγ).
Figure 6E:
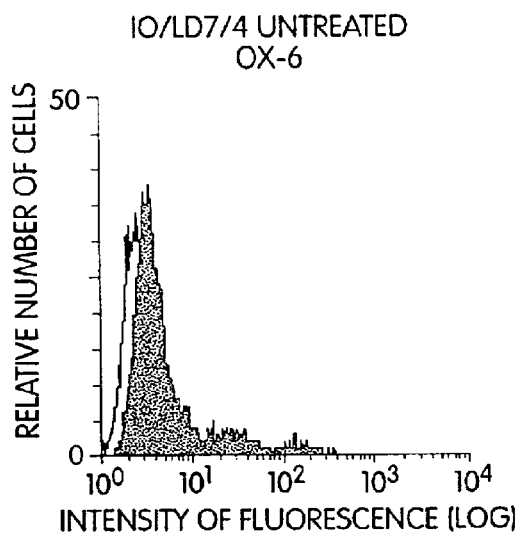
FIG. 6E is a graph showing the expression of the adhesion molecule OX-6 in the IO/LD7/4 clone in the absence of induction by interferon gamma (IFNγ).
Figure 6F:
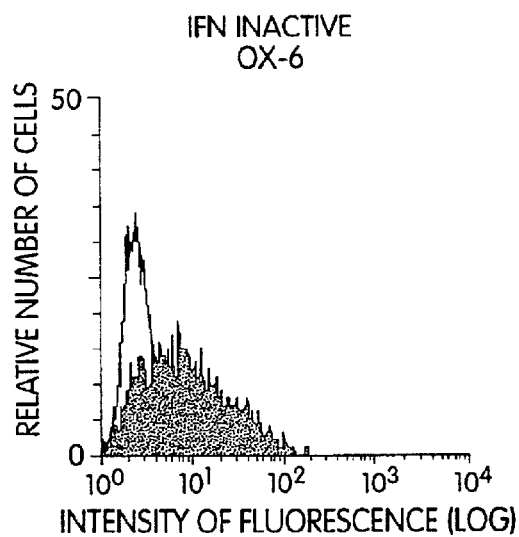
FIG. 6F is a graph showing the expression of the adhesion molecule OX-6 in the IO/LD7/4 clone in the presence of induction by interferon gamma (IFN-γ).

(3) Expression of the T-antigen. The retinal pigment epithelial cells with extended life-span (selected with the aid of G418) showed substantial nuclear staining in the presence of antibodies directed against the T-antigen (FIG. 3B), whereas no staining was observed with the retinal pigment epithelial cells in primary cultures.

(4) Expression of retinal pigment epithelial markers. The primary cultures of retinal pigment epithelial cells and the IO/LD7/4 clone expressed the antigen specific for the retinal pigment epithelial cells, namely RET-PE2 (FIG. 5). Furthermore, the expression of the cytokeratins, which were normally used to identify retinal pigment epithelial cells, was present to the same extent in both the primary cultures and the cells with extended life-span, as illustrated in the flux cytometry analysis (FIG. 5).

(5) Expression of the antigens of the major histocompatibility complex. All the pigment epithelial cultures showed a constitutive expression of the class I major histocompatibility antigens (OX-18, see, FIG. 4, FIG. 6, and FIG. 7), which was induced by 100 U/ml of rat recombinant IFNγ for 24 hr.

Both the primary cultures and the retinal pigment epithelial cells with extended life-span were incapable of expressing the antigens of the class II I-A or class II I-E major histocompatibility complex. However, after 5 days of activation, there was a weak but significant expression of both I-A (FIG. 6 and FIG. 7) and I-E.

Figure 7A:
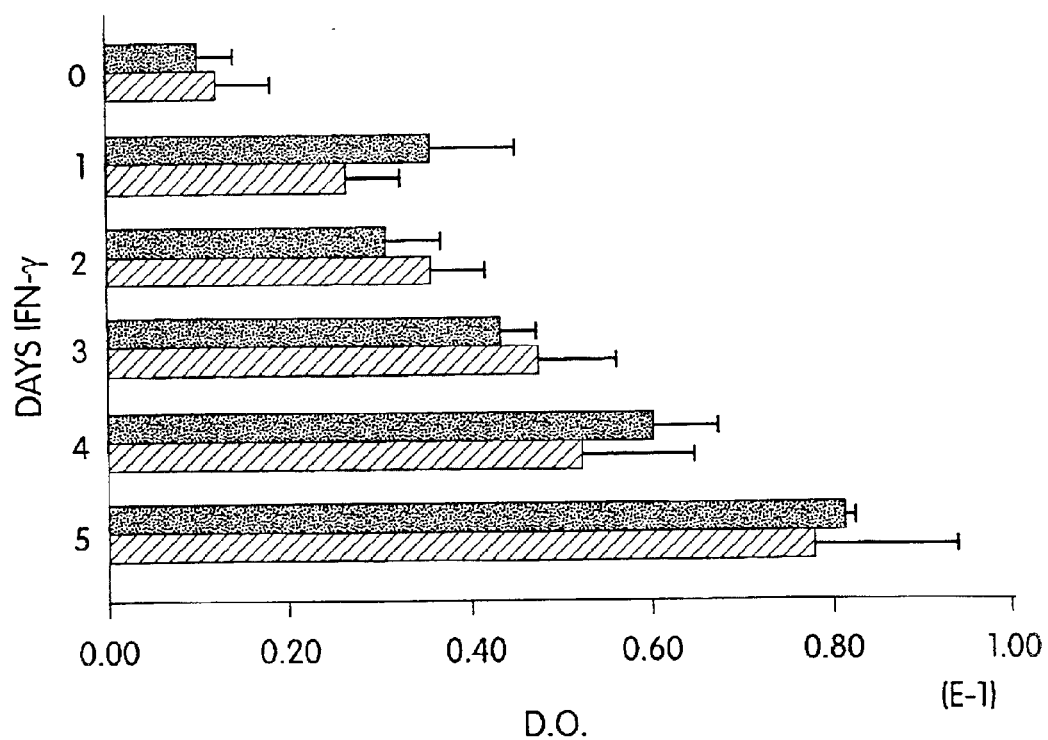
FIG. 7A is a bar graph showing, for the IO/LD7/4 cells, the expression of class II I-A histocompatibility antigens (black) and I-E histocompatibility antigens (shaded) in response to IFNγ from 0 to 5 days.
Figure 7B:
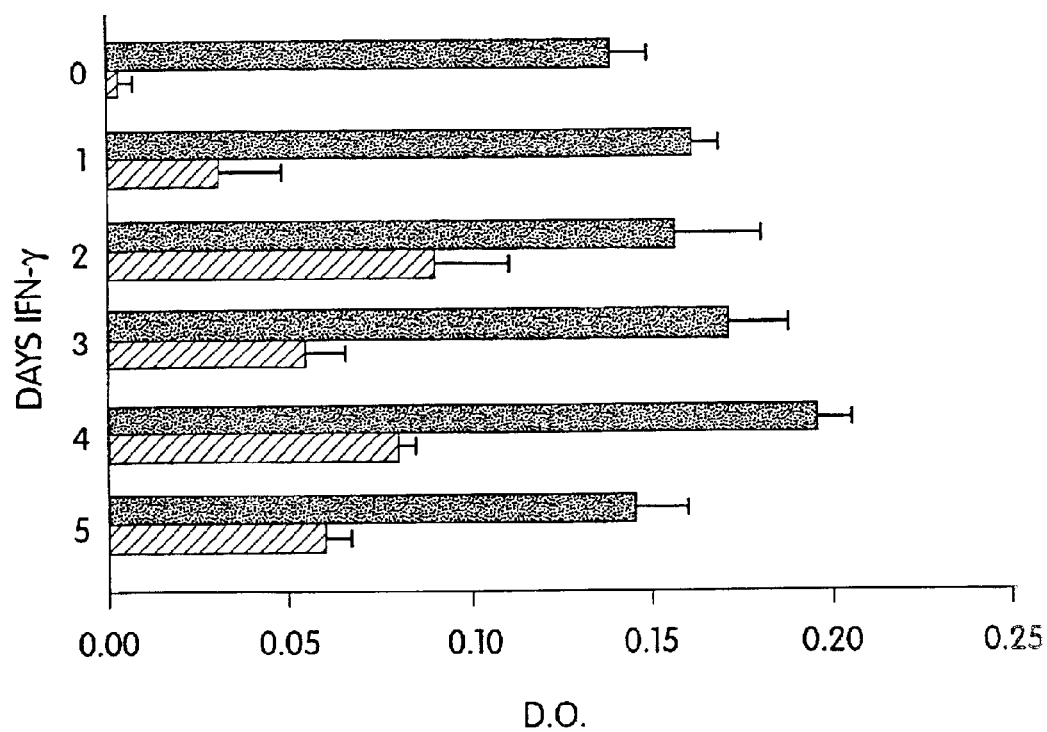
FIG. 7B is a bar graph showing, for the IO/LD7/4 cells, the expression of the adhesion molecules VCAM-1 (shaded bars) ICAM-1 (black bars) in response to IFNγ from 0 to 5 days.

(6) Expression of the adhesion molecules. The primary retinal pigment epithelial cell cultures and cultures of retinal epithelial cells with extended life-span did not constitutively express VCAM-1, but after 3–5 days of activation with IFNγ, low levels of expression were observed (FIG. 7).

(7) Migration of the T-lymphocytes across the monolayer. The migration across the monolayers of primary retinal pigment epithelial cells and retinal pigment epithelial cells with extended life-span differed significantly. The primary cells exhibited a degree of migration (38±3%) which was significantly greater than that of the IO/LD7/4 cells (17±2%, p <0.01) (FIG. 8).

(d) Phagocytosis of external segments of the rods by the IO/LD7/4 cells in vitro.

(1) Method. IO/LD7/4 cells were cultivated to the point of confluence on Thermanox® slides in 4 wells of tissue culture plates. The medium was sucked off and replaced with a medium containing a suspension of dissociated adult retinal cells. 24 hr later, the retinal suspension was removed and then the slides were rinsed and treated for observation under the electron microscope. The cells were also cultivated on slides coated with Matrigel®, rinsed, fixed and stained with cresyl violet.

Figure 9:
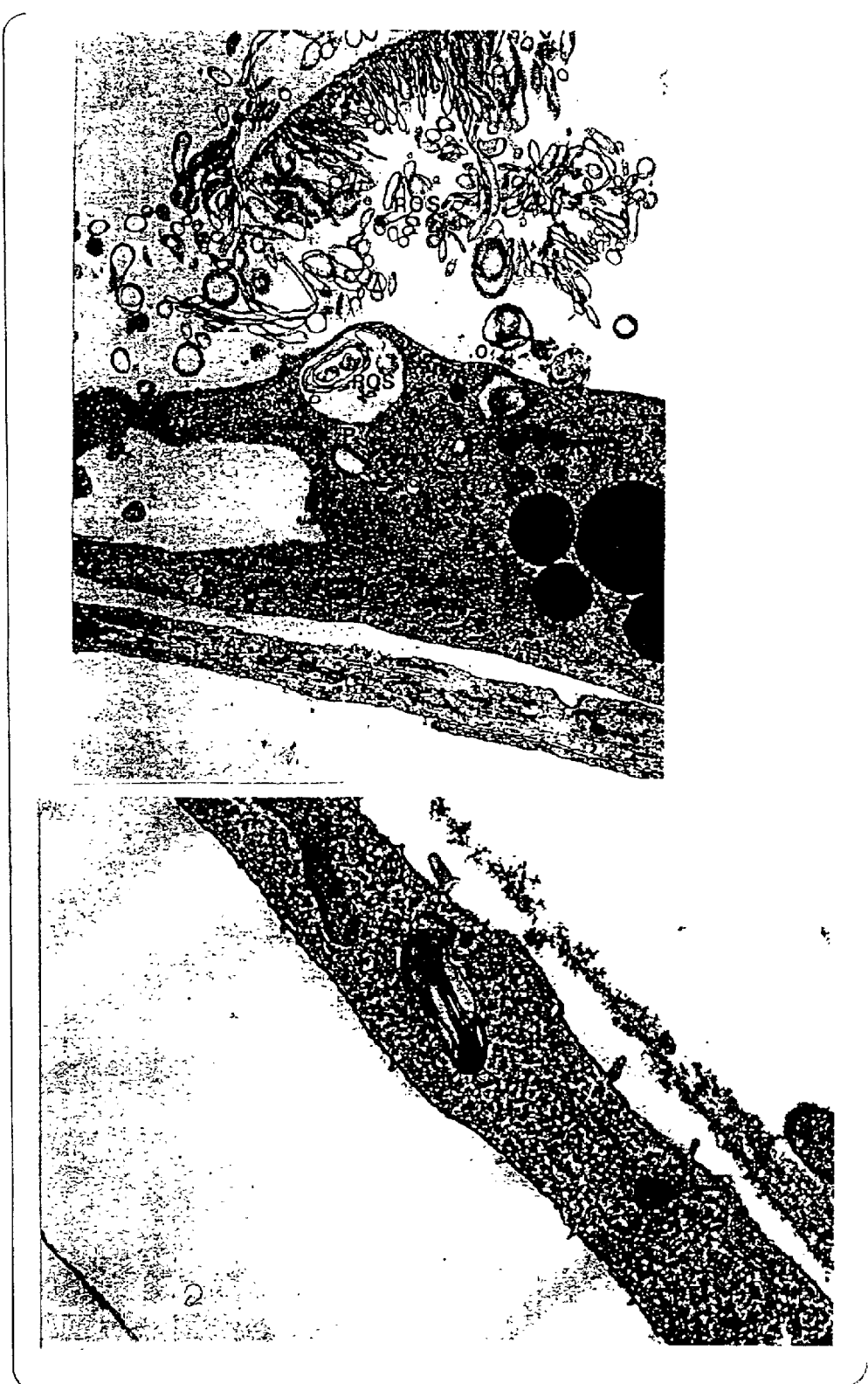
FIG. 9 is a set of electron micrographs of IO/LD7/4 cells co-cultivated with dissociated retina; the debris of external segments (ROS) is adjacent to the cells and found in the phagosomes (P).
Figure 10:
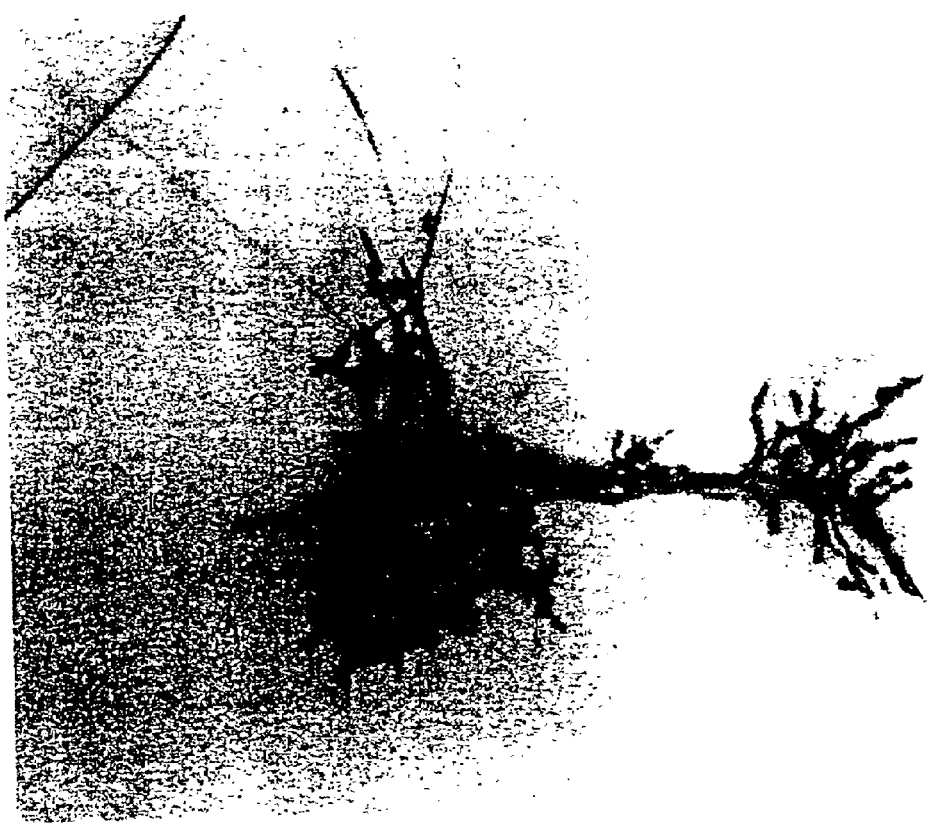
FIG. 10 is a micrograph showing IO/LD7/4 cells cultivated on slides coated with Matrigel®. The cells show a high contractile capacity, creating stress lines in the matrix.

(2) Results. The presence of retinal material (external segments of photoreceptors) dissociated in the phagosomes can be distinguished in the electron micrographs of IO/LD7/4 cells. External segments were identified both in suspension above the primary retinal pigment epithelial cells and in the phagosomes. A thin layer of electronically dense material was observed under the layer of cells in culture and was interpreted as corresponding to a basal membrane produced by the cells (FIG. 9). The cells cultivated on Matrigel® caused a contraction of the matrix (FIG. 10).

EXAMPLE 4

Implantation of IO/LD7/4 Cells in the Subretinal Space

The retinal pigment epithelial cells with extended lifespan of the invention were implanted in the subretinal space. These cells make it possible to save the photoreceptors from degeneration and are a particularly advantageous source of donor cells.

(a) Pilot experiment: grafting of IO/LD7/4 cells in Sprague-Dawley rats and RCS rats.

(1) Methods. IO/LD7/4 cells were injected into the subretinal space of 8 anaesthetized 12-week-old Sprague-Dawley rats and six 4-week-old RCS rats. The eye was rotated towards the nose and anchored; an incision was made with a very fine scalpel (micro surgical knife with an angle of 150) through the scleroid and choroidal layers in order to facilitate the insertion of a micropipette. The cells ($2 \times 10^5/\mu l$) were injected into the subretinal space using a micropipette attached to a 10 $\mu l$ Hamilton syringe. Half the group was treated orally with cyclosporin (2.1 mg/rat/day) throughout the experiment.

The rats in each group were anaesthetized with a lethal dose of anaesthetic (Euthatal®) and then an intracardiac perfusion was carried out successively with phosphate-buffered saline and a tissue fixative; the animals were then enucleated. The eyes were cryoprotected and included in OCT® (Tissue-Tek; Miles), a cryoprotection agent.

A series of sections were prepared (14 $\mu m$ thick) and stained with cresyl violet and with a monoclonal antibody directed against the SV40 T-antigen and against PCNA (proliferative cell nuclear antigen).

(2) Results. No tumor formation was observed in the eyes of animals which had received grafts of IO/LD7/4 cells. No immune response was observed in the eyes of animals which had not received an immunosuppressive treatment.

Figure 11:
FIG. 11 is a micrograph showing the hexagonal morphology of the cells obtained after grafting the IO/LD7/4 cells onto the retina of Sprague-Dawley rats.
Figure 12A:
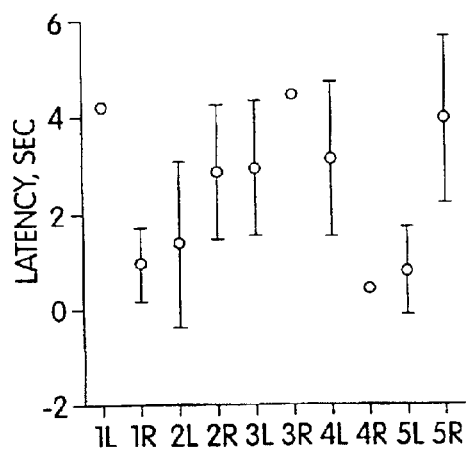
FIG. 12A is a graph showing the means and standard deviations of the latency times of the pupillary reflexes in response to a light stimulus in rats grafted with primary retinal pigment epithelial cells.
Figure 12B:
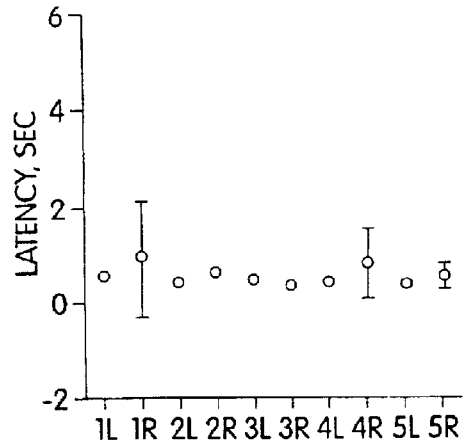
FIG. 12B is a graph showing the means and standard deviations of the latency times of the pupillary reflexes in response to a light stimulus in rats grafted with IO/LD7/4 cells.
Figure 12C:
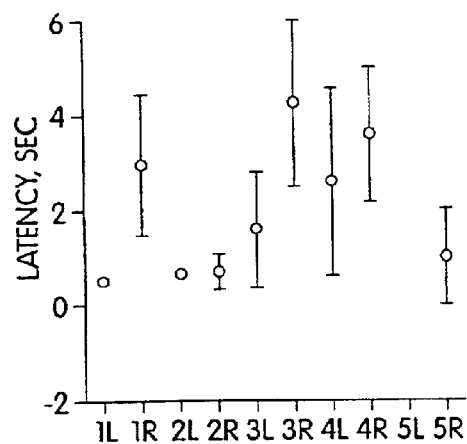
FIG. 12C is a graph showing the means and standard deviations of the latency times of the pupillary reflexes in response to a light stimulus in control animals (blank operation)
Figure 12D:
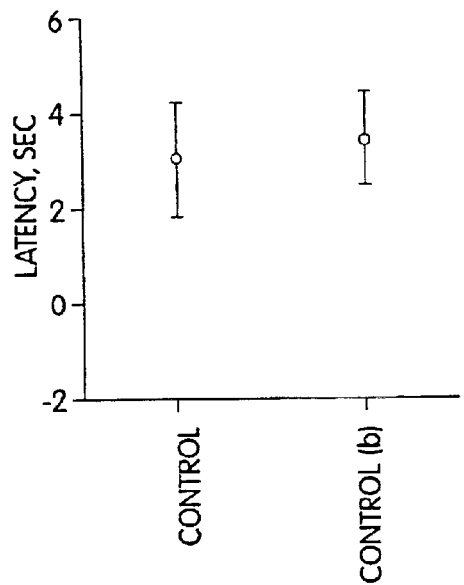
FIG. 12D is a graph showing the means and standard deviations of the latency times of the pupillary reflexes in response to a light stimulus in r dystrophic ROS rat as a function of age; the mean latency time of a non-dystrophic rat is 0.48±0.04 second; L=left eye and R=right eye.
Figure 13A:
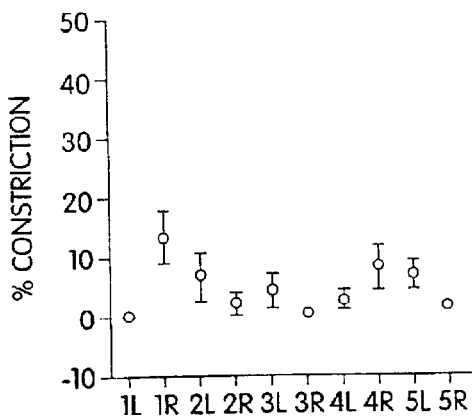
FIG. 13A is a graph showing the means and standard deviations of the amplitude of the pupillary reflex responses to light in rats grafted with primary retinal pigment epithelial cells.
Figure 13B:
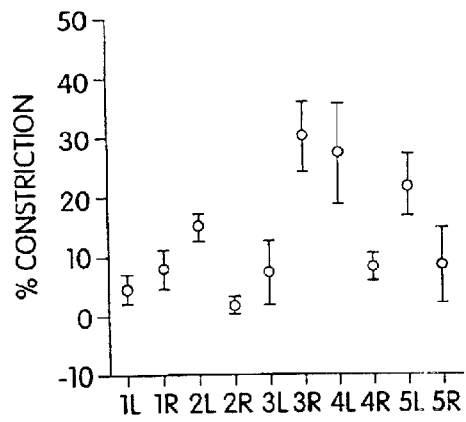
FIG. 13B is a graph showing the means and standard deviations of the amplitude of the pupillary reflex responses to light in rats grafted with IO/LD7/4 cells.
Figure 13C:
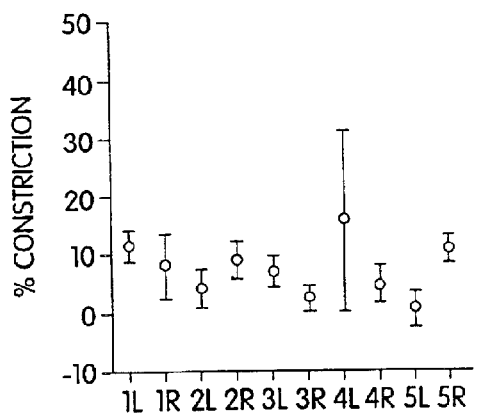
FIG. 13C s a graph showing the means and standard deviations of the amplitude of the pupillary reflex responses to light in control rats.
Figure 13D:
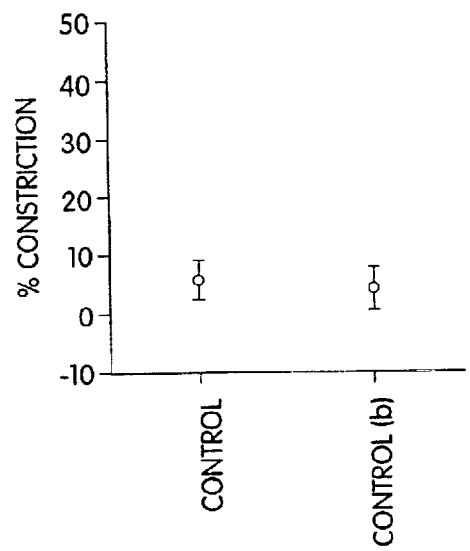
FIG. 13D s a graph showing the means and standard deviations of the amplitude of the pupillary reflex responses to light in a dystrophic RCS rat as a function of age. The mean amplitude of response of a non-dystrophic 6-month-old animal is 19.7±5.7%; L=left eye and R=right eye.

In the majority of sections, the epithelial cell layer was a single layer (monolayer), but a multilayer was observed in certain regions. When the blocks were sectioned the cells of the invention possessed in viva the hexagonal phenotypic characteristics of the primary retinal pigment epithelial cells, even though these characteristics were lost in vitro (FIG. 11). This result was clear when the transplant has more than one layer of cells.

Protection of the photoreceptors was observed in all the retinas of RCS rats which had grafts of IO/LD7/4 cells. All the sections stained with the antibodies directed against the SV40 T-antigen and PCNA were negative.

(b) Comparison between grafts of freshly harvested primary retinal pigment epithelial cells and grafts of IO/LD7/4 cells on the visual function.

(1) Methods. Eleven dystrophic RCS rats (3–4 weeks old) were grafted either with primary retinal pigment epithelial cells or with IO/LD7/4 cells by injection into the subretinal space of each eye, as described in (a) above. A separate group of animals was injected with medium only (control operation).

(2) Evaluation of the pupillary light reflex (PLR). The PLR was recorded with a pupillometer 6 months after transplantation: the animals were tested under anaesthetic (halothane/nitrous oxide). The light stimulus was presented for 3 seconds (sec); the data were collected with an ISCAN pupillometer and the latency and amplitude of the response were recorded.

(3) Results. The latency time of the PLR responses of the animals which had received a graft of IO/LD7/4 cells was significantly shorter than that of the animals which had received a graft of primary retinal pigment epithelial cells or an injection of medium (FIG. 12). The amplitude of the responses exhibits large variations in the different groups. However, a subset of animals which had received IO/LD7/4 cells shows a greater amplitude of response than the other groups (FIG. 13).

(4) Behavioral evaluation of the visual acuity. To evaluate the capacity of the rats to detect visual images, the rats were placed in a large cage whose walls can be changed (plain walls or decorated walls). Two rats were present in each cage during the test The rats' activity was measured for 5 min. In a first stage, the animal explores its environment and gets accustomed to it. In a second stage, the activity of the animal increases only if the walls were changed. If the visual environment was the same, the activity was not modified. The extent of the animal's activity can consequently be used as an index of its visual detection and its visual acuity.

Figure 14:
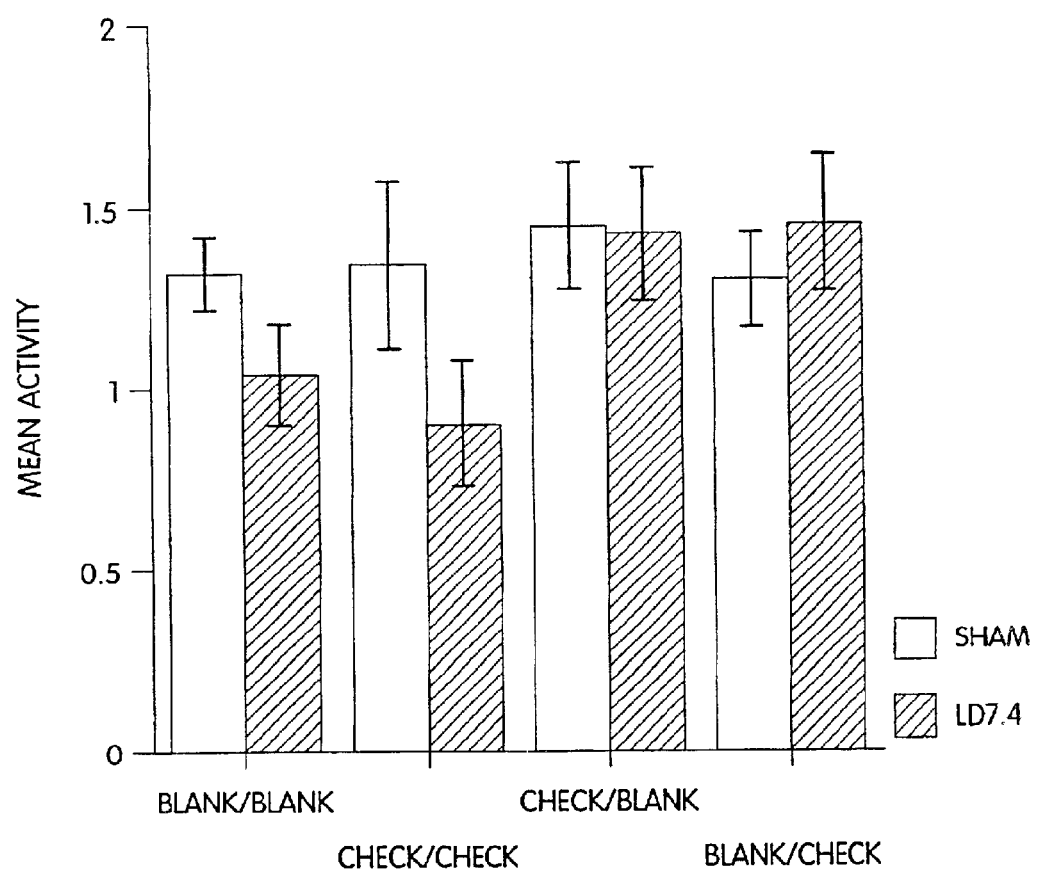
FIG. 14 is a bar graph showing the modifications of the mean activity of rats placed in cages with walls of different designs; rats grafted with IO/LD7/4 cells (shaded bars), control rats (blank operation or sham; white bars); blank= plain walls; check=decorated walls.

(5) Results. The capacity of the dystrophic rats to detect the variations in their visual environment decreases over a period of 3 months. The exploratory activity of the rats grafted with IO/LD7/4 cells was high in the second part of the test, i.e., when the environment has been modified (plain walls changed to decorated walls or vice-versa) (FIG. 14).

Figure 15:
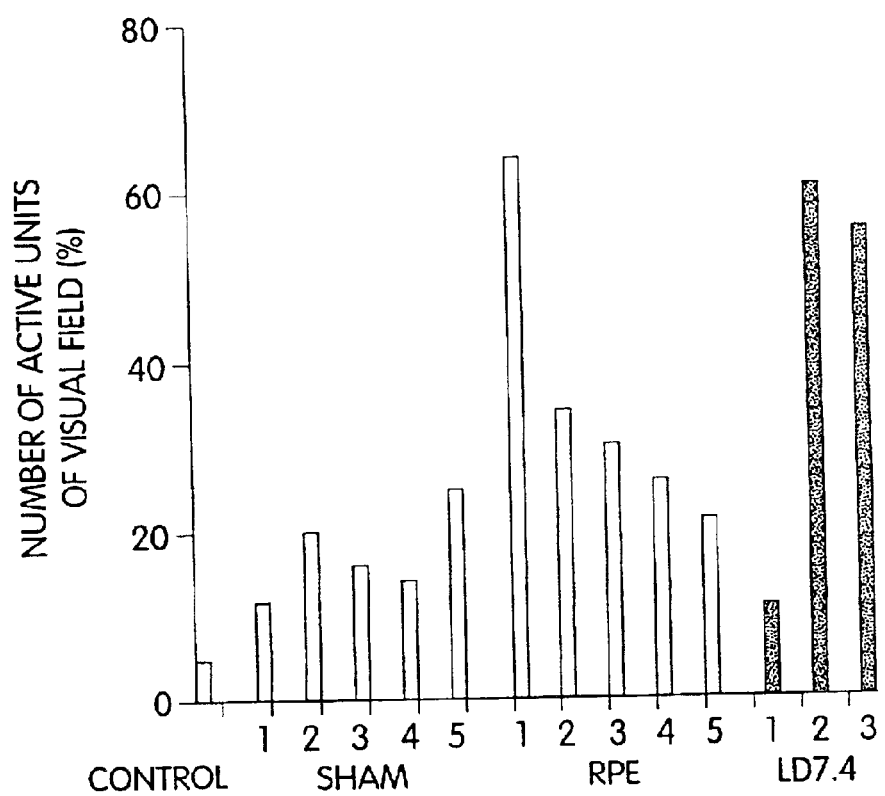
FIG. 15 is a bar graph showing the number of active units of visual field in the superior colliculus, expressed as a percentage of the number of active units of visual field; the IQ/LD7/4 and primary retinal pigment epithelial (RPE) cells are capable of slowing down the loss of visual field in the grafted animals compared with the non-grafted animals (control or sham).
Figure 16:
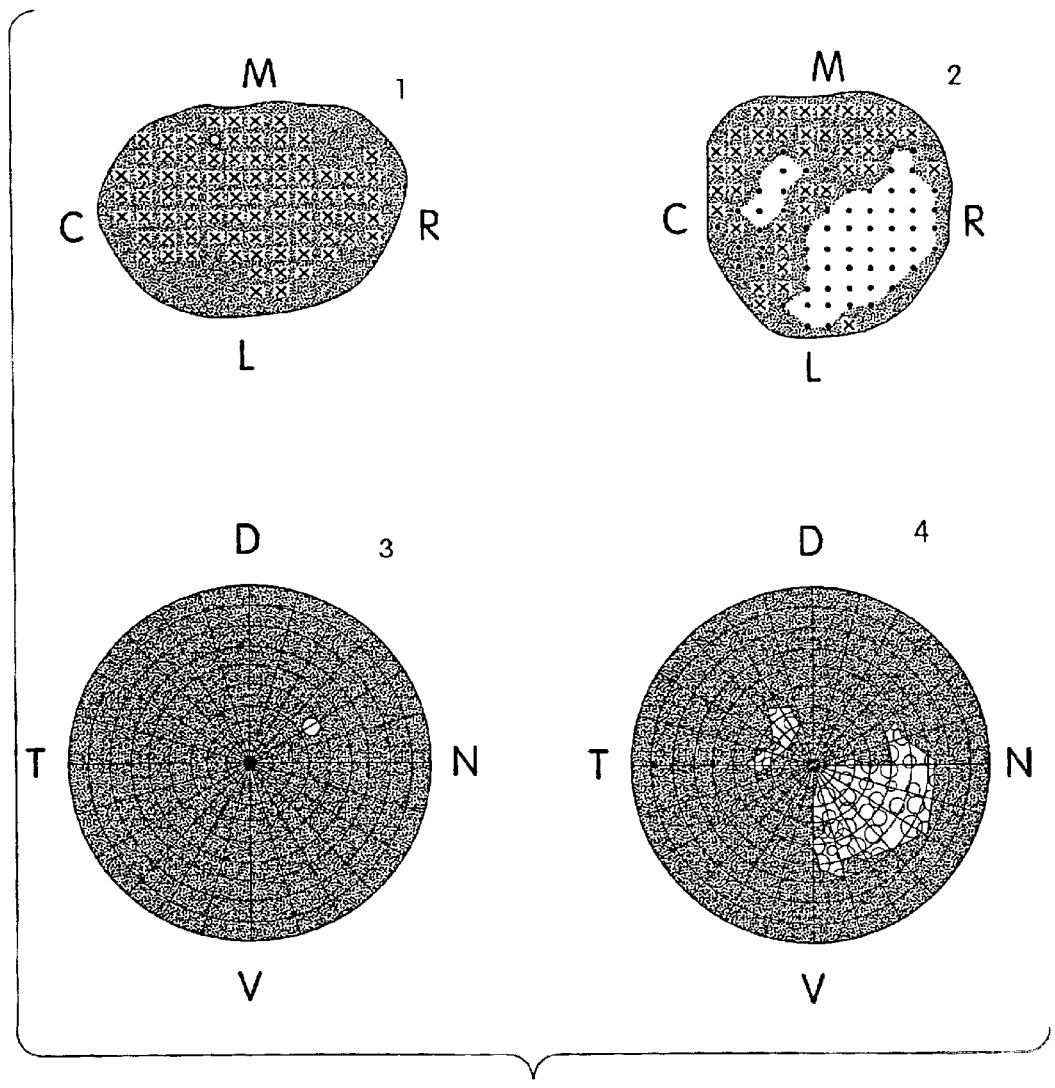
FIG. 16 is a representations of recordings showing, on the one hand, a 2-dimensional view of the superior colliculus (FIG. 16A and FIG. 16B, in which C=caudal, M medial, R=rostral and L=lateral), and on the other hand the maps of the corresponding visual fields of the retina (FIG. 16C and FIG. 16D, in which D=dorsal, N=nasal, V=ventral and T=temporal). The crosses on the map of the colliculus represent the zones for which no recording could be obtained. The dots correspond to the zones for which recordings could be obtained; the left-hand panels represent the recordings of a dystrophic 6-month-old rat. The recordings could be made from a single unit (light zone), which is typical of animals of this age. The right-hand panels represent the recordings of a rat grafted with IO/LD7/4 cells on the superior temporal retina. It is observed that responses can be obtained from a wide zone of the superior colliculus.
Figure 17A:
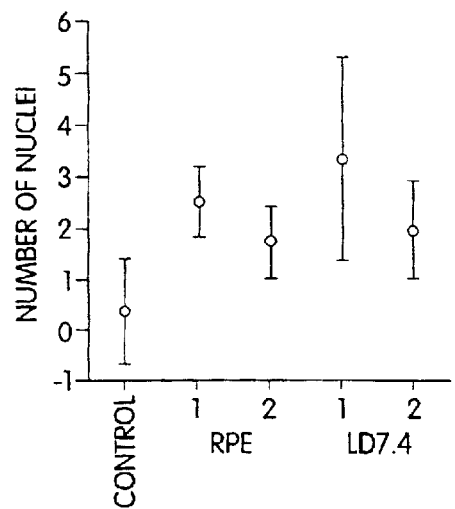
FIGS. 17A–D are a set of graphs showing some of the differences relating to the histological characteristics of the retinas of rats grafted with primary retinal pigment epithelial (RPE) cells or IO/LD7/4 cells. The number of nuclei in the outer nuclear layer is shown in FIG. 17A. The number of nuclei in the inner nuclear layer is shown in FIG. 17B. The depth of the outer plexiform layer in $\mu$m is shown in FIG. 17O. The relative zone (%) of retinas saved by grafting is shown in FIG. 17D.
Figure 17B:
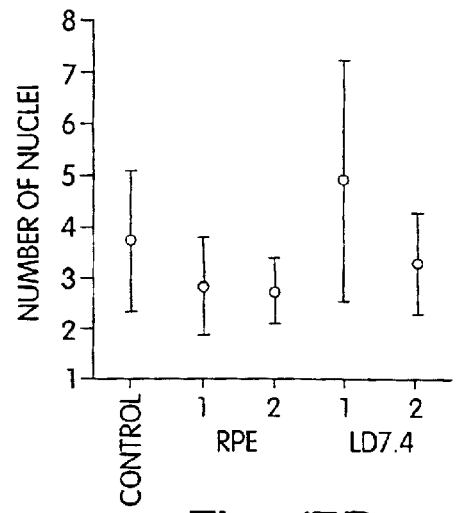
Figure 17C:
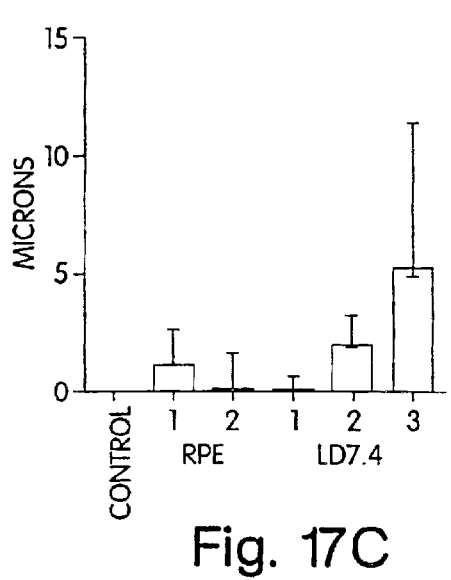
Figure 17D:
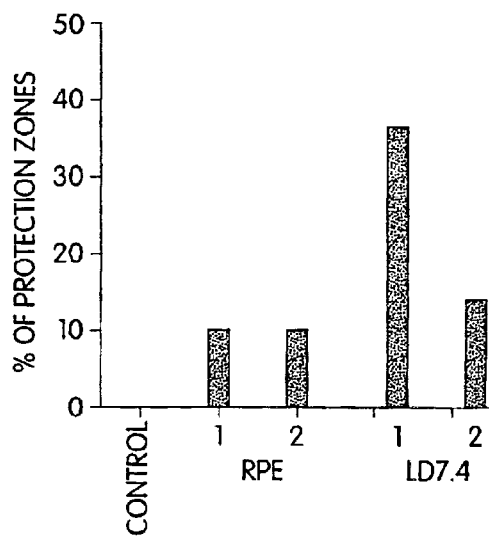

(6) Electrophysiological evaluation. The head and eyes of the anaesthetized rats were immobilized by means of a stabilizing apparatus and sutures, respectively. The superior colliculus contralateral to the stimulated eye was exposed. The animals were adapted to a light level of 0.34 candela/$m^2$ for 1 hr before recording in order to enable the cones and rods to be evaluated simultaneously. The rat was orientated to face a translucent hemisphere (Ganzfield radius of 55 cm) so that the tested eye was at the center. The stimuli, comprising a fixed light 3° in diameter and 5.8 candela/$m^2$ in intensity, were projected onto the surface of the hemisphere. Different receptive fields (multi-unitary or single) were recorded from the layer nearest the surface of the superior colliculus (SC) (about 200 μm from the surface of the superior colliculus) using glass-coated carbon fiber electrodes. The recordings cover the whole of the superior colliculus on the basis of a grid system with a pitch of 200 μm corresponding to 10°–15° in the visual field (FIG. 15 and FIG. 16).

(7) Results. The axons of the retina project onto the superior colliculus in a precise and topographic manner; consequently, modifications in the recordings obtained from the superior colliculus do indeed reflect the changes which had occurred in the retina (FIG. 15). A small scotoma begins to develop after 6 weeks in the dystrophic rats; it occupies half the visual field after 3 months and includes the whole of the retina after 6 months. The primary retinal pigment epithelial and IO/LD7/4 grafts slow down this deterioration of the visual field. The grafts of IO/LD7/4 cells appear to be the more effective.

(8) Morphological evaluation of the prevention of the loss of photoreceptors after the grafting of primary retinal pigment epithelial cells. Four eyes which had received either primary retinal pigment epithelial cells or IO/LD7/4 cells were examined. Using an image analysis software in association with a microscope (DMR, Leica), the thickness of each of the cellular layers of the retina was measured on the dystrophic 6-month-old rats and the number of nuclei in the inner and outer nuclear layers was counted. The proportion of retina saved was estimated.

(9) Results. After 6 months, no layer of photoreceptors was observed in the dystrophic rats. A few cells exist in this zone and can be considered as vestiges of photoreceptors. The grafts of cells with extended life-span showed large regions of saved cells in 6-month-old animals. The proportion of retinal zone saved by the grafts of primary retinal pigment epithelial cells was 6% and 13.8% with an outer nuclear layer (ONL) having a thickness equal to 3 strata of nuclei, whereas the percentage of retina saved by the grafts of IO/LD7/4 cells was 27.9% and 36.3% with an ONL having a thickness equal to 5 strata of nuclei. An important difference between these sections was the presence of a distinct external plexiform layer in the eyes grafted with IO/LD7/4 cells (FIG. 17).

(c) Migration of the IO/LD7/4 cells in vivo.

(1) Method. Fifteen dystrophic 4-week-old rats were grafted with fluorescent IO/LD7/4 cells. 10 of the recipient rats were grafted on both eyes; the other 5 rats were grafted on one eye only. The animals (2 with a transplant on both eyes and one with a transplant on one eye only) were sacrificed 3, 7, 14, 28, 42 and 98 days after grafting by administration of a lethal dose of anaesthetic (intracardiac perfusion in the presence of phosphate-buffered saline). The animals were enucleated and the eyes were fixed in 4% paraformaldehyde for 6 hr. The tissue was cryoprotected and included in OTC. Sections were prepared (14 μm thick) and made up into 3 series.

Series A was stained with cresyl violet. Series B was stained with an anti-microglia antibody; the series were examined under a fluorescence microscope.

(2) Results. The labeled cells were located in all the grafted eyes up to 14 days after the operation, but were more difficult to identify later because of elimination of the marker. If the staining was clearly visible, the labeled cells occupy up to 30% of the retina. Staining of the adjacent sections with cresyl violet confirms the action of the grafts on the saving of photoreceptors in all the transplants.

EXAMPLE 5

Further Work with Rat Retinal Pigment Epithelial Cell Line, IO/LD7/4

IO/LD7/4 grafts rescue photoreceptors in the area of transplantation. Even with survivals of more than 6 months, pathological responses to the grafts were minimal. Tests have been exploring potential hazards by implantation to abnormal sites e.g., brain and under extreme conditions. While the cells grafted into the brain appear to follow basal laminae, implanted cells in the retina do seem to be localized within the region of the subretinal space.

We have assessed functional efficacy. Two approaches have been used, (1) behavioral and (2) physiological. The behavioral studies have been directed at using an efficient screening method and to this end considerable attention has been given to head tracking to moving stripes of different frequencies up to 0.5 cycles /degree. In unoperated dystrophic RCS rats, head tracking cannot be elicited after 8 weeks of age (FIG. 20). In sham operated animals, the cut-off occurs around 11 weeks. In dystrophic rats with IO/LD7/4 transplants, head tracking, even to 0.5 cycles/ degree stripes persists for at least 5 months postoperative (FIG. 21). Animals placed in a pattern recognition box also perform well although controls fail. Acuity testing was done, prior to cortical physiology.

Physiological studies have focused on mapping visual field by recording from the superior colliculus. In the earlier studies, we used standard conditions and measured the development of a partial scotoma. In new experiments, we have established a baseline luminance condition where even in normal rats; no response can be elicited. The amount of increase in luminance, measured in log candela/m$^2$, needed to produce a threshold response was measured and recorded for each position. Maps are shown in FIG. 22, where even at 5 months post-transplantation, a small sham effect can be seen, but in transplanted animals, two typical examples of which are shown in FIG. 22. There was a reasonable area of rescue corresponding to the general position of the graft. Detailed correspondence of graft location, photoreceptor rescue and functional rescue was performed.

EXAMPLE 6

Production of Mammalian RPE Cells

Mammalian retinal pigmentary epithelial (RPE) cells are prepared as follows: An expression vector, which is a plasmid or a retroviral vector, containing the SV-40 T gene is produced. This expression vector is associated with a selection marker such as the puromycin resistance gene. Primary RPE cells are transfected with the expression vector and selected using puromycin. Parental lines are obtained by selection of the resistant colonies. With a retroviral vector, the incubation time for the RPE cells with the medium containing the retroviral vector is 2 hr at 37° C. The other conditions are the same as described in EXAMPLE 2.

EXAMPLE 7

Production of Human Primary RPE Cells

Human primary RPE cells are isolated and cultured as shown in EXAMPLE 5. The cells are then transfected with a mixture of Fugene 6 (Roche), a transfection reagent including a blend of lipids (non-liposomal formulation) in 80% ethanol (Cotten et al., 1 Gene Therapy 239–246 (1994); Remy et al., 5 Bioconjugate Chem. 647–654 (1994)) and a plasmid DNA with a ratio of 1 µg of plasmid DNA for 3 µg of Fugene. The plasmid DNA expression vector contains a gene such as E1A and preferentially a selection marker such as neomycin resistance gene. Incubation time with the Fugene/plasmid DNA mixture is 48 hr at 37° C. under a $CO_2$ atmosphere. After incubation, selection will start using either neomycin at a concentration of 800 µg per ml or puromycin at a concentration of 1 µg/ml. Parental lines are obtained by selection of the resistant colonies.

EXAMPLE 8

Human RPE Cell Lines

For this EXAMPLE, more than 100 clones with extended life-span were established from a human eye. These clones were screened for appearance, antigenicity and expression patterns to see how similar they might be to normal retinal pigment epithelial cells. Of a collection of 12 clones, 2 particularly normal looking ones (clone 7 and clone 116) were studied further behaviorally. The first group of these cells were transplanted into twenty 3–4 week old dystrophic RCS rats. The cells have been shown to elicit robust head tracking at higher frequency stripes, not seen in controls, and to rescue visual field responsiveness over a substantial area of the superior colliculus (FIG. 23 and FIG. 24). Anatomical investigation of those animals has shown good local photoreceptor rescue and no evidence of abnormal pathology.

EXAMPLE 9

Tumorigenicity Test of hRPE Clones in Nude Mice

The objective of this EXAMPLE was to assess, in nude mice, the potential tumorigenicity of 2 distinct clones of human HRPE cells transfected with a construct bearing the large T antigen of the SV40 virus (see, EXAMPLE 9).

As required for such testing (according to FDA recommendations), the grafting procedure include a reference cell line as a control. The U87 (human glioblastoma) cell line was used as a positive control reference cell line. In addition, we decided to irradiate the nude mice to fully discard possible interference with some immune competent cells (NK, macrophages) able to impair the survival of grafted cells.

Two clones of human RPE cells were selected based on morphological and antigen expression criteria (see, EXAMPLE 3). Clone number 7 was transfected with a plasmid pVIM TΔt (thermosensitive). Clone number 116 was transfected with a plasmid pVIM T (non-thermosensitive). For these 2 clones, the oncogene was under the control of the vimentin promoter. The 2 clones were at passage number 13 when subcutaneously grafted in nude mice.

The grafting procedure was as follows: After trypsinisation, rinsing, cells were resuspended in the serum-free graft medium (phosphate-buffered saline 0.1 M, sucrose 10 mM) at the concentration of 50,000 cells/µl. 200 µl of suspension (10 millions cells) were then injected subcutaneously in the right flank of nude male mice of 8 weeks of age (Iffa Credo, n=10 for each RPE cell line, n=5 for the U87 cell line) under gaseous anesthesia with a mixture of isoflurane 1–2% in ⅓ oxygen/⅔ azote. These nude mice were irradiated at the dose of 5 µrad 2 days before the grafting procedure.

Tissue processing was performed as follows: Animals were observed daily for 3 weeks and 5 animals per cell line were killed at this time point under anesthesia (acepromazine+ketamine) by intracardiac perfusion of PFA, 4% diluted in phosphate-buffered saline 0.1 M. The other 5 animals were perfused 12 weeks later. Skin of the right flank was dissected, the graft site identified, and a subsequent immersion in the fixative was performed overnight. After cryoprotection 24 hr in sucrose 20% in phosphate-buffered saline 0.1 M, the pieces of skin were included in OCT® (Tissue-Tek; Miles), frozen in isopentane, and stored at −20° C.

For histological examination, cryostat sections of 14 µm thick were performed and air dried. A hematoxylin/eosin coloration was performed as follow: Slides were dehydrated in increasing concentrations of ethanol (75, 95, 100, 100%) and inversely rehydrated up to water, stained in Mayer's hemalun (ready to use, RAL) for 10 min. Sections were rinsed quickly in water, differentiated in alcohol/acid (1.5 ml HCl 35.5% in 1000 ml ethanol 95%) for 15 to 20 sec, and rinsed again in water for 5 min. Sections were subsequently stained 10 min in eosin orange G solution (1% each in water), rinsed in water for at least 30 min and checked under microscope. Sections were finally dehydrated through ascending ethanol concentrations, cleared in xylene and mounted in Eukitt medium.

The Schmorl technique was performed as follows: air-dried slides were rehydrated in water, immersed in a solution composed in volume of 75% (ferric chloride 1%), 10% (potassium ferricyanide 1%), 15% distilled water, up to maximum 5 min. The coloration was monitored by microscopic observation every 30 sec intervals. When desired the sections were washed in water, dehydrated in ascending ethanol concentrations, cleared in xylene and mounted in Eukitt. Varying shades of blue stains lipofuscins, melanin, chromaffin cells, sulfhydryl groups.

The results of the EXAMPLE were that injection of 200 µl of the cell suspension produced a visible mass on the flank of the animals. After a swelling period of the graft zone between days 3 to 6 for hRPE 7 and 116, the size of the mass progressively decreased and became invisible on the surface of the skin. The tumors of the U87 control grafted animals grew up continuously.

Five animals of each hRPE cell lines 7 and 116 were perfused 3 weeks post-implantation. No palpable mass was detected on the flank of these animals, and the injection point was easily identified in the internal side of the skin because the clumps of cells exhibited a yellow-brown coloration (see, FIG. 25). At the histological analysis on hematoxylin/eosin stained sections these clumps were constituted of brown/yellow cells with a nucleus of normal aspect (see, FIG. 26). The Schmorl reaction produced a blue/green coloration of the cells in the graft mass (see, FIG. 27A).

The remaining animals (n=5 for hRPE 7 and 116 clones) were studied 15 weeks following transplantation. For hRPE 7 no palpable mass was detected in the 5 animals and the injection point was again identified by the persistence of a small brown stain at the interface between skin and the underlying tissue in 3 of 5 animals. For the 2 other mice, no pigmented stain was detected. For hRPE 116, no palpable mass was detected in the 5 animals. The site of injection was again located by its coloration in the internal side of the skin in 4 of 5 animals.

The number of yellow/brown cells was strongly reduced in comparison with the 3 weeks time period. This drastic reduction in the number of blue/green cells is also visible on the Schmorl stained sections (see, FIG. 27B).

Concerning the 3 perfused control animals, all of them developed a tumor at 3 weeks. The 2 remaining mice had to be killed 40 days post transplantation because of the increasing size of the tumors (1.31 g and 2.84 g).

This EXAMPLE shows that no particular pathogenicity was apparent and all control animals developed a tumor with the reference cell line. Pigmentation or coloration of the grafted cells localized in the internal side of the skin was only seen for the hRPE transplanted animals and not for the controls. The pigmented cells were likely the transplanted hRPE because this yellow/brown coloration persists in the animals sacrificed 12 weeks later (15 weeks post-graft). Contaminant infiltrating immune competent cells (which are also colored if present) would probably have disappear from the graft site after such a period of time.

After a short post-implantation period of swelling of the implantation zone probably due to reactive edema, the hRPE 7 and 116 clones do not develop tumors in the flank of irradiated nude mice after a period of 15 weeks.

EXAMPLE 10

Rescue of Visual Function by Transplantation of Human Retinal Pigment Epithelial Cells to the Retinae of RCS Rats The RCS (Royal College of Surgeons) rat has a retinal pigment epithelial cell defect which leads to progressive degeneration of the adjacent photoreceptors. RCS rats are genetically predisposed to undergo significant visual loss due to a primary dysfunction of retinal pigment epithelial (RPE) cells. Such rats present an in vivo bioassay for human age-related macular degeneration. In this EXAMPLE, this animal was used as a bioassay to explore the use of human retinal pigment epithelial cells with extended life-span, which when transplanted into the subretinal space of the eye not only prevent photoreceptor loss but also preserve a range of visual responses studied behaviorally and physiologically. Thus, such cells may provide a suitable and convenient source for transplantation in related human diseases such as age-related macular degeneration.

This EXAMPLE shows that retinal pigment epithelial cells with extended life-span derived from either human or rat sources can preserve vision in an animal with a disease that has some commonality with age-related macular degeneration. Such a preparation provides an effective bioassay for testing grafted cells. Thus, a major limitation to using cell transplantation to correct age-related macular degeneration, a suitable source of donor cells, can be overcome by the use of a carefully characterized cell type with extended life-span. Such cells have the additional advantage of being suitable targets of ex vivo gene therapy prior to transplantation.

Background. Age related macular degeneration (AMD) is responsible for 54% of blind registrations in the UK over 65 years of age and 11% of patients between 16 and 65 years. In the USA 14% of the population over 40 years suffer visual impairment due to AMD (Evans et al., 28 Health Trends 5 (1996); Rehmani et al., 103 Ophthalmology 1721 (1996)) and there are indications that its prevalence is increasing. Currently there are no reliable treatments available. This disease appears to be due to defects associated with the retinal pigment epithelium (RPE) (Zarbin, 8 Eur. J. Ophthalmol. 199 (1998)). Consistent with this hypothesis is the reported improvement in vision following surgical translocation of the retina to an area of healthy RPE, demonstrating the importance of functional RPE in this condition (Zarbin, 8 Eur. J. Ophthalmol. 199 (1998)). Although this approach offers some therapeutic possibilities, it is highly invasive and the complex surgical procedure which is only appropriate in a limited number of cases. A far less traumatic approach, and one that has wider clinical application, is the re-population of the macular region with transplanted RPE cells. This strategy has been tested in the RCS rat model in which there is a genetic dysfunction of the RPE cells leading to photoreceptor cell death and thus serves as a model for human AMD. Using this model, studies have shown that the implantation of freshly harvested syngeneic RPE cells from non-dystrophic rats into the subretinal space of young recipients reduces subsequent photoreceptor cell loss (De Juan et al., 125 Am. J. Ophthalmol. 635 (1998); Lewis et al., 128 Am. J. Ophthalmol. 135 (1999)). These transplantation strategies offer considerable promise, but are subject to a number of logistical, ethical and safety problems that limit their broader application in human clinical therapy. In particular, major restrictions are imposed by the limited supply of donor eyes (Lund et al., 29 Ophthalmic Res. 305 (1997)) and the finite numbers of phenotypically stable and functional RPE cells that can be harvested from primary culture. Furthermore, the impracticality of performing full safety testing on primary cultures from every donor, such as for retroviruses and prions, would further limit their widescale clinical use. Despite these problems, the grafting of RPE as a possible therapy has attracted substantial experimental interest, with several studies reporting improved photoreceptor survival (Li & Turner, 47 Exp. Eye Res. 911 (1988); Lopez et al., 30 Invest. Ophthalmol. Vis. Sci. 586 (1989); Li & Turner, 52 Exp. Eye Res. 669 (1991)). What has yet to be clearly demonstrated, however, is whether this approach is capable of significantly preserving vision.

Experimental design and methods used in investigating this EXAMPLE. A general plan was followed in the series of assays as follows:

(1) Specific cell types, some of which were labeled in vitro, were transplanted as suspensions into the subretinal space of young dystrophic RCS rats.

(A) Cell types and preparation.

(i) Primary cultures of human retinal pigment epithelial cells.

These cultures were used as a reference group for using the human cell line, partly providing baseline material and partly establishing what immune suppressive precautions need to be taken. Primary human retinal pigment epithelial cells were obtained from donor eyes. Briefly, the posterior eyecup was isolated from the rest of the eye and the retina gently teased away from the underlying retinal pigment epithelial cell monolayer and rinsed in 0.02% EDTA. The posterior eyecup was then dissected into 3 segments and areas of retinal pigment epithelial cells isolated by cloning rings. Retinal pigment epithelial cells were then trypsinized with 0.25%/0.02% EDTA in calcium-magnesium free phosphate-buffered saline for 45–60 min with occasional trituration, until retinal pigment epithelial cells dissociated from Bruch's membrane. Cells were then seeded onto tissue culture plastic dishes pre-coated with fetal calf serum, and left to adhere for 10 min followed by the addition of culture medium consisting of Ham's F-10, 20% fetal calf serum, 2 mM L-glutamine and 100 IU/ml penicillin and 100 µg/ml streptomycin. After transplantation, eyes were fixed.

(ii) Human cell lines. A number of different clones have been established expressing different molecules. Here we have focused on cells from two human hRPE clones, 7 and 116 cells (see, EXAMPLE 8). We have shown that in vitro these cells express all the important molecules attributable to normal retinal pigment epithelial cells.

(iii) Human cell lines derived from cells that have been transfected with genes for specific molecules. The genes for specific molecules can include green fluorescent protein, molecules involved in suppressing the immune response, suicide genes, and genes for growth factors such as ciliary neurotrophic factor (CNTF) and basic fibroblast growth factor (bFGF).

(iv) Human cell lines derived from cells that have been immortalized spontaneously. Among the cells that can be used according to the methods of this EXAMPLE are ARPE-19 cells (American Type Culture Collection (ATCC) Number CRL-2302), which are normal retinal pigmented epithelial (RPE) cells and express the retinal pigmentary epithelial cell-specific markers CRALBP and RPE-65. ARPE-19 cells form stable monolayers, which exhibit morphological and functional polarity. The ARPE-19 cell line is stable and has been isolated from a primary culture of a donor eye without genetic manipulation. Under certain culture conditions the cells can become senescent (Dunn et al., 62 Exp. Eye Res.155–69 (1996)).

(B) Transplantation technique. Human RPE cells (see, EXAMPLE 8) were transplanted to young (3–4 weeks) old dystrophic RCS rats as a suspension containing about $2 \times 10^5$ cells/$\mu$l. The eye was proposed for injection. A scleral incision next to pars plana was made temporally with an ophthalmic knife. Two ml of the cell suspension was injected into the subretinal space through the scleral incision with a fine glass micropipette. The procedure was visualized with an operating microscope through a dilated pupil and a specially adapted contact lens was used to permit visualization of the fundus. The cornea was punctured to limit efflux of cells. Immediately after injection, the fundus was examined to check for retinal damage or signs of vascular distress. At this stage, transplants were scored as to relative success; this correlates well with later outcome. The animals were examined 1 week post-transplantation to check that the detachment had recovered. As controls, some animals received injection of medium; others remained unoperated. Cells were checked for viability at the beginning and end of a transplantation session.

(2) Monitoring. The progress of the injected cells was followed by in vivo monitoring and in short-term and long-term histological and immunocytochemical studies. Retinae from animals that had been used for electrophysiology were also processed for histology.

(3) Behavioral screening. Grafted animals were tested with basic behavioral screening methods to gain some measure of functional efficacy. Simple visual reflexes deteriorate in the RCS rat, although many persist for long periods. We have shown that acuity responses also diminish. Using the RCS rat, one can examine visual reflexes that can be maintained by transplants; these served as a very effective screening method for experimental manipulations. More important was how much cortical visual function was preserved and whether experimental animals could "see" as a result of transplantation.

(A) Experimental protocol. Five weeks post-transplantation rats were screened using a simple behavioral test (ongoing studies have shown that RCS rats do not show diminished function with these tests compared with normal controls until 8 weeks of age). Some rats were then studied anatomically, others were taken through pattern recognition and acuity tests, followed by cortical physiology studies. In all cases, controls were included in these groups and were coded throughout the EXAMPLE so that the person testing did not know to which group they belong.

In the initial tests, animals were fully tested to establish whether performance on the relatively simple screening test correlated in any way with the degree of sophisticated vision that could be rescued. If such a correlation was be made, then one could rely on the initial screening to assess whether new clones were more or less effective.

(B) Behavioral screening. Prior to testing for cortical function, animals were quickly screened for transplant efficacy. We used a head turning behavior to square-wave gratings in a revolving drum (optokinetic). This test had been adapted for use in this EXAMPLE. The test can discriminate normal and dystrophic rats by 8 weeks of age; transplanted animals may not show the deteriorated response seen in dystrophies. Optokinetic following to gratings of 0.5, 0.25, and 0.125 cycles/degree moving clockwise and then anti-clockwise was video taped (following for each eye was in a temporal to nasal direction). The amount of time the animals spent following the gratings was assessed. We than correlate any changes in optokinetic behavior with the animal's visual acuity.

(C) Visual discrimination. Following the initial testing, animals were next screened on a simple pattern discrimination task, using activity as an index of whether or not the animal can detect patterns on the walls of the box. Animals were placed in a box first with completely blank walls. The animal's activity was monitored for 5 min at which point it will be removed temporarily from the arena while a patterned stimulus was placed on the walls. The animal was returned to the arena for a further 5 min. Normal rats can detect a change in the environment and attend to it. This behavior is detected as an increase in the animals' motor activity. Three-month-old dystrophic animals cannot discriminate patterns; but after retinal pigment epithelial transplantation their performance was improved. This test has been simplified by using an automated test box using a computer controlled system for monitoring activity much like that already in place for the photophobia studies.

(4) Physiological assessment of graft efficacy; Visual field analysis. Most animals from step (3) were then examined to see how visual cortical single cell physiology was affected both in the degenerative phase and after transplantation. Under urethane anesthesia (1.25 g/kg) the test eye was immobilized using 6-0 sutures attached to the is frame, and the pupil was dilated with topical tropicamide as before. Corneal clouding was prevented using a non-corrective contact lens. Animals were dark-adapted for 1 hr at 0.34 candela/m$^2$ (mesopic range) prior to recording from the superficial layers of the superior colliculus contralateral to the experimental eye. Single and multi-unit recordings were made covering the full extent of the superior colliculus along a rectilinear grid of 200 $\mu$m periodicity. Where a response to whole-field illumination was found, units responsive to stimulation of discrete receptive fields (RFs) were tested. In cases where a receptive field can be defined (180 candela/m$^2$, spot illumination), static stimuli were presented to its center. Presence or absence of responsiveness to standard receptive field illumination (5.8 cdandela/m$^2$) was confirmed by assembling post-stimulus time histograms (5 msec bins) over 30 consecutive stimuli, using inter-stimulus intervals varying from 3 sec to 20 sec in order to minimize adaptation. At the end of recording a map of the visual field as projected onto the superior colliculus was obtained.

(5) Physiological assessment of graft efficacy; Anatomical analysis. After physiology, the retinae were studied further anatomically. A group of about 15 animals at a time was used for each experimental run. Eight received cell transplants, 5 received sham injections of carrier medium and 2 served as unoperated controls. For behavioral studies, only one eye was injected. For anatomical studies, both eyes usually were injected, one often being the sham. Each set was followed through blind. At the end of an assay, the data was analyzed statistically (if appropriate) and, if necessary, additional groups with the same treatment were followed through. If the results were clear-cut, either positive or negative, a test can usually be completed with 2 runs. Individual animals used for functional assessment can usually also be used for anatomical work, so reducing numbers.

(6) Summary of results. We have generated clones of SV40 T-transfected retinal pigment epithelial cells which showed many of the features of normal retinal pigment epithelium. When transplanted to the subretinal space of 1 month old RCS rats, subsequent photoreceptor degeneration was reduced, and visual responses in the superior colliculus were preserved. When tested for visual tracking to moving stripes, normal RCS rats failed to follow after about 8 weeks of age, while cell transplanted animals continued tracking up to at least 5 months of age. In addition the transplanted animals continued to respond in a pattern recognition test. Over the postoperative time period studied (4 months) there was no evidence of abnormal behavior of the transplanted cells.

EXAMPLE 11

Subretinal Transplantation of a Genetically Engineered Human RPE Cell Line Prevents Visual Loss in the RCS Rat Subretinal transplantation of an extensively characterized, genetically engineered human RPE cell line (hRPE7), which expresses SV40 large T antigen and exhibits an extended in vitro life span, results in a significant preservation of visual responses as assessed using both behavioral and physiological criteria. This visual improvement correlates with photoreceptor survival. These results demonstrate the potential of genetically modified human RPE in therapeutic transplantation strategies for retinal degenerative diseases.

In this EXAMPLE, we have overcome two fundamental obstacles associated with transplantation strategies for the treatment of AMD. Firstly, the problem of sourcing sufficient numbers of safe human RPE cells for grafting has been addressed by the use of a carefully characterized cell line that has been genetically modified to extend its in vitro life span. This manipulation enables these cultures to undergo an extensive number of cell doublings thus producing a large bank of pathogen-free and phenotypically identical cells for use in transplantation protocols. Secondly we have demonstrated the efficacy of the human cell grafts not only through histological appraisal of photoreceptor survival, but also by demonstrating preservation of visual function using behavioral and physiological analysis. Here we show for the first time that a human RPE cell line grafted into the subretinal space of the RCS rat results in a significant preservation of vision over a 5-month post-operative period.

Primary cultures of human RPE cells derived from a donor eye were genetically modified to extend their in vitro life span and, after extensive cloning and characterization, a single clone designated hRPE7 was selected for subretinal transplantation into RCS rats. For the donor eye, human RPE cells were cultured from a human eye obtained from a fully consented 50 year-old female Caucasian donor under local ethics committee approval. Upon receipt of the tissue the anterior segment, iris and lens were removed, and the posterior segment stored overnight in sterile culture medium at 4° C. Vitreous and neural retina was gently removed and the eyecup dissected into three segments. Cloning rings were placed on the exposed RPE layer and cells rinsed with 0.02% EDTA for 5 min. 0.25%/0.02% trypsin/EDTA was placed into the cloning rings and incubated at 37° C. for 45 min to allow RPE detachment from the underlying Bruch's membrane. RPE cells released by gentle trituration, were seeded onto tissue culture flasks and culture medium was added. Culture medium consisted of Ham's F-10, 20% heat inactivated fetal calf serum, 2 mM L-glutamine, 100 U/ml penicillin, 100 $\mu$g/ml streptomycin (Gibco/ Life Technologies, Scotland, UK) and 1 $\mu$g/ml amphotericin-B (Boehringer Mannheim, Germany). Medium was changed every 2–3 days and all cells were cultured at 37° C. in 5% $CO_2$. Primary cultures were genetically modified to extend their in vitro life-span by transfection with a construct encoding SV40 large T-antigen which was deleted for the small T-antigen (pVIM T$\Delta$t) along with RSVpuro (which encodes a puromycin resistance gene). Clones were established by selection in 1 $\mu$g/ml puromycin and by limiting dilution of parent lines.

Figure 28:
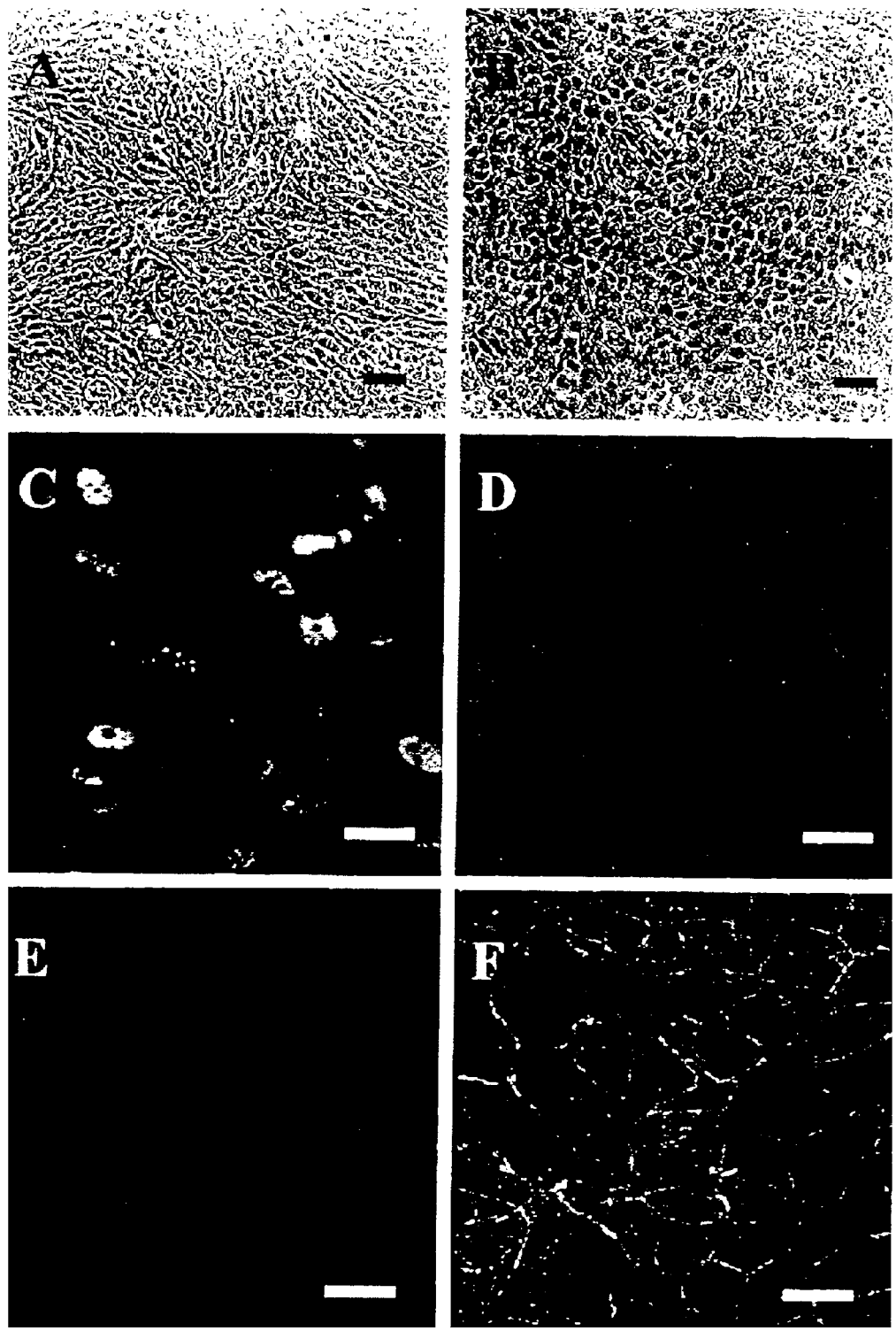

Clone hRPE7 was selected since this cell line exhibited a non-transformed phenotype and expressed characteristic epithelial and RPE specific markers (FIG. 28). Independent assessment of phenotypic cell transformation was performed following subcutaneous injection of 10 million hRPE7 cells into irradiated athymic mice. After 3 weeks hRPE7 cells failed to produce tumors unlike U87 human glioblastoma cells that were injected as a positive control. hRPE7 cells also failed to form aggregates or foci when plated into soft agar. Cytogenetic analysis demonstrated an essentially diploid karyotype. Clone hRPE7, as well as other clones of genetically modified human RPE, were screened for the expression of SV40 large T antigen, cytokeratins (8 and 18) and for the junctional protein zonula occludens-1 (ZO-1). Cell monolayers were fixed with either 3.7% paraformaldehyde (for detection of ZO-1 and SV40 large T antigen) or cold acetone/methanol (1:1; for cytokeratins). After washing and blocking with serum primary antibodies against SV40 large T antigen (hamster polyclonal ascites; gift from M. Baratin, Paris), ZO-1 (rabbit polyclonal; Zymed), and cytokeratins 8 and 18 (mouse monoclonal, clone NCL-5D3, Novocastra Laboratories) were added for 1 h. Cells were washed again and serum blocked again prior to the addition of the appropriate fluorophore-conjugated secondary antibody. Following a 1h incubation cells were washed and mounted for viewing on a Zeiss epifluorescence or confocal laser scanning microscope. Positive mRNA expression of RPE65, pigment epithelial derived factor (PEDF) and cellular retinaldehyde-binding protein (CRALBP) was also demonstrated by reverse transcriptase PCR in hRPE7 cells.

hRPE7 cells were transplanted into the dorso-temporal subretinal space of 3–4 week old dystrophic pigmented RCS rats, at a stage prior to the occurrence of any significant cell death. Cultures of hRPE7 cells were trypsinized, washed and delivered in suspension ($2 \times 10^5$ per graft) in 2 $\mu$l of Ham's F10 medium through a fine glass pipette (internal diameter 75–150 $\mu$m) inserted through the sclera of anaesthetised animals. Cell viability remained at >90% as assessed by trypan blue exclusion. During the postoperative period the animals were carefully monitored and the local retinal detachment caused by the graft resolved within several days. Animal care was in accordance with institutional and government guidelines.

Sham injected rats received carrier medium alone. A total of 20 rats received successful grafts and 5 had sham injections. All animals were maintained on oral cyclosporin A (210 mg/l of drinking water) from 2 days before transplantation until sacrifice. Five grafted rats were allowed to survive for 5 months post-operatively with the remainder being sacrificed at earlier time points for anatomical assessment of short-term changes associated with transplantation. A further 6 non-operated age matched dystrophic and 3 non-dystrophic RCS rats provided appropriate cyclosporin treated controls.

Efficacy of transplants in preventing visual loss was monitored by assessment of head-tracking performance to moving stripes of different spatial frequencies (Cowey & Franzini, 35 Exp. Brain Res. 443 (1979)). The head tracking apparatus consisted of a circular drum, which rotated at a constant velocity of 12°/sec around a stationary holding chamber containing the animal. The inner surface of the drum was lined with removable stimulus panels. The panels consisted of black and white high contrast square wave gratings. Three gratings of different spatial frequencies were used: 0.125, 0.25 and 0.5 cycles/degree. A video camera mounted above the apparatus recorded head movements. A test period consisted of 4, one-minute sessions of rotation interspersed by non-rotating intervals. The direction of rotation was varied such that by the end of the test period the animal had experienced 2×1-minute rotations in a clockwise direction and 2×1-minute rotations in an anti-clockwise direction. The responses observed in rotation of the chamber clockwise and anti-clockwise were summed to obtain a single score indicating the total duration of head turning for a particular grating. Animals were tested 10 and 20 weeks postoperatively. A single operator conducted all assessments blind and codes were broken upon completion of all data acquisition.

Analysis of head tracking performance revealed a distinction between graft and sham injected animals by 10 weeks postoperatively (FIG. 29). Behavioral data was analyzed using an analysis of variance (2 way ANOVA with repeated measures). Post-hoc analysis was performed on factors that were shown to be significant from the ANOVA. For statistical analysis of the physiological data, both a randomization test and a t-test were used to compare hRPE7 thresholds against sham thresholds. Both statistical procedures produced identical results. The graphical representation of the statistical analysis was derived from the randomization results.

Both non-dystrophic animals and dystrophic animals who received a transplant of hRPE7 were able to track all grating stimuli and were significantly better than sham operated and non-operated dystrophic control animals (FIG. 29). By 20 weeks postoperatively, sham operated controls were unable to track a visual stimulus whilst hRPE7 transplanted animals performed as well as non-dystrophic animals when tracking a visual stimulus of 0.125 cycles/degree. At a grating of 0.25 cycles/degree grafted animals tracked significantly better than both sham operated and dystrophic animals although at 0.5 cycles/degree this ability was lost. Thus, hRPE7 transplanted animals were able to track visual stimuli at both 10 and 20 weeks postoperatively in contrast to both sham operated and dystrophic animals.

The head tracking method used here for the first time in RCS rats has the advantage of discriminating dystrophic from non-dystrophic rats as early as 8 weeks of age. This makes it an effective, compact and non-invasive screening method for following the progress of changes in visual responsiveness with time. Sham injections prolong functional deterioration, perhaps by flushing debris from the subretinal space as well as by possibly provoking growth factor production, but by 10 weeks post-transplantation the effect of the graft was clearly distinguishable from the sham effect.

After head-tracking performance was completed, visual performance was studied electrophysiologically. The threshold sensitivity response to light was used to define the area of visual field rescue. Animals (under terminal urethane anesthesia, 1.25 g/kg i.p.) were individually tested at 20 weeks post-graft by recording multi-unit extracellular activity in the superior colliculus to illumination of respective visual receptive fields. This procedure was repeated for 76 independent points (spaced 200 μm apart, each step corresponding to approximately 10°–15° displacements in the visual field), together covering the whole visual field. Visual thresholds were measured as the increase in intensity over background (maintained at 0.02 candela/m$^2$ to minimize rod saturation) required for activating units in the superficial 200 μm of the superior colliculus with a spot of light 3° in diameter. Data gathered from each point gave a global image of the eye.

Figure 30:
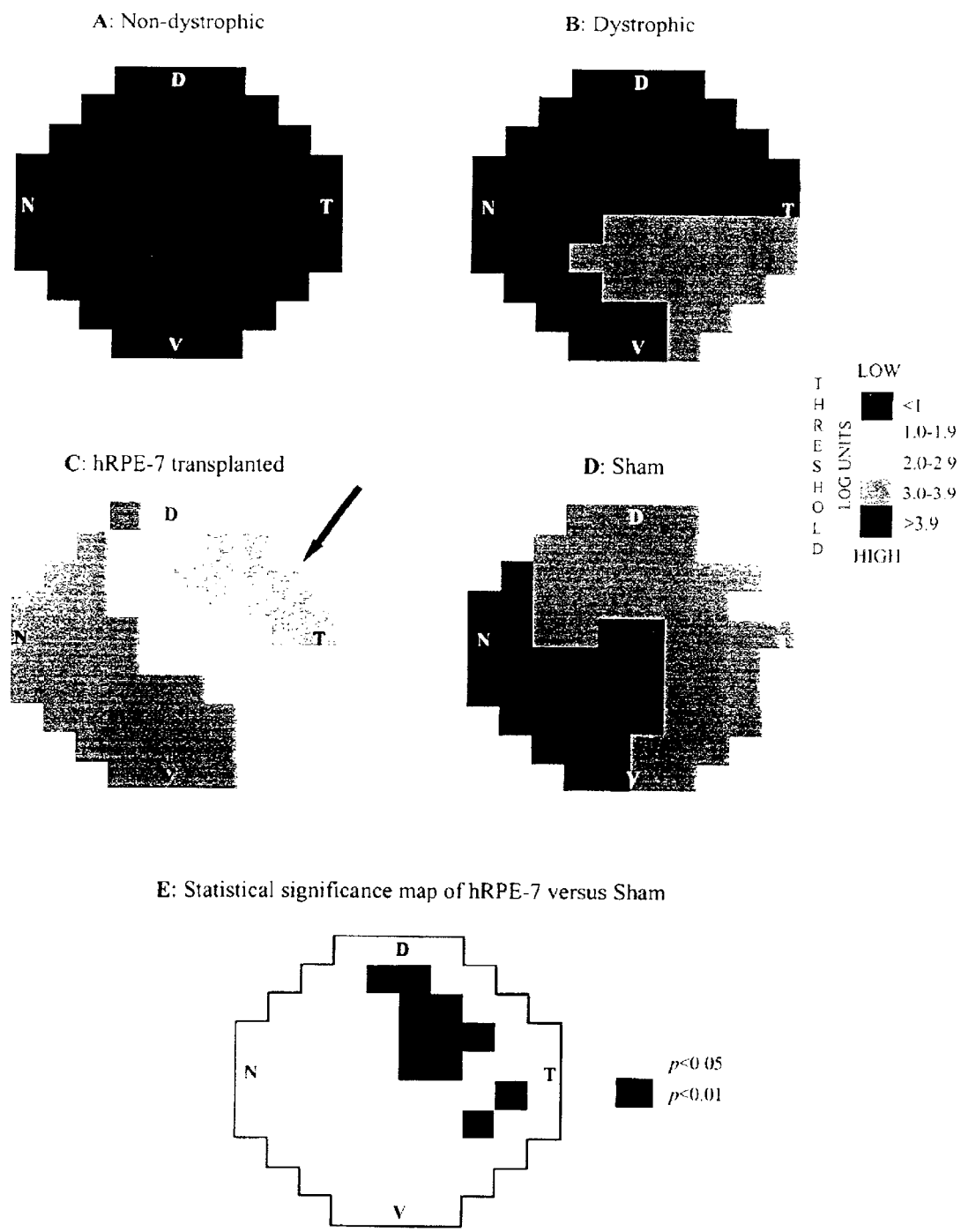

In non-dystrophic rats visual thresholds did not exceed 0.7 log candela/m$^2$ above background (FIG. 30). By contrast, in non-operated dystrophic rats, the thresholds were of the order of 4 log units. Sham-injected rats showed some highly localized functional rescue in the temporal retina with lowest thresholds at 2.6 log units on average maps. However, the hRPE7 transplanted rats exhibited substantially greater levels of visual preservation with thresholds of 1.6 log units on average maps (several points were associated with 0.7 log units thresholds). The precise region of maximal sensitivity varied slightly between animals, due to small variations in the siting of the graft, leading to higher values when superimposing individual maps to obtain averages. When the grafted retinae were averaged, 52% of the area was associated with thresholds lower than 3.0 log, and 16% with thresholds lower than 2.0 log units, while in sham injected retina these proportions were only 7% and 0% respectively. When significance between the sham and hRPE7 injected rats was determined, 29 of the 76 points analyzed showed a significant improvement in visual function ($p<0.05$) (FIG. 30). The area of maximal rescue invariably tended to be confined to the region of cell injection.

Threshold sensitivity studies used here have not been previously applied to this model and provide an indication of relative preservation of visual field. Its importance lies in the fact that the data collected compares with visual field perimetry testing in humans (Massof & Finkelstein, 18 Invest. Ophthalmol. Vis. Sci. 263 (1979)). A reliance on functional assessment is clearly preferable when providing background to clinical treatments, since it is not clear what relation commonly used measures such as thickness of photoreceptor layer have to degree of functional rescue. Furthermore, ERG which has been used previously to assess visual function is known to correlate poorly with visual capacity in retinitis pigmentosa patients.

Histological evaluation of the retina was carried out on control and hRPE7 grafted animals at one, three and five weeks, and at 4 and 5 months post-transplantation. Animals were euthanized using Euthatal (Rhône Merieux, UK) and perfused transcardially with PBS followed by periodate-lysine-paraformaldehyde (PLP). Eyes were embedded in polyester wax and 8 μm thick section cut through the retina. Sections were stained with cresyl violet (BDH, UK) and mounted with DePeX (Merck/BDH, Lutterworth, UK). Sections were viewed and photographed on a Leica DMRB microscope under bright field illumination.

Figure 31:
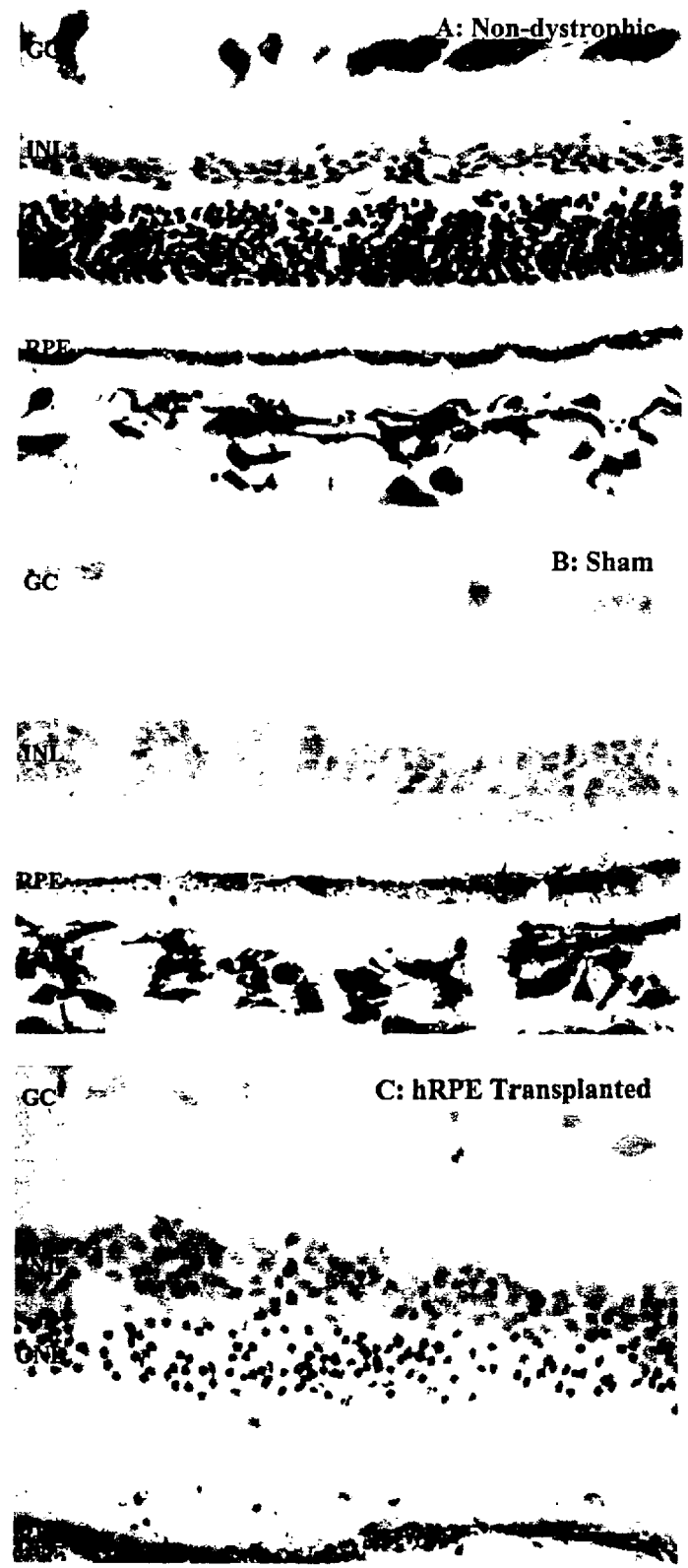

At short postoperative survival periods there was evidence of graft cells sitting in the subretinal space with no sign of untoward inflammatory responses. Histological analysis of non-dystrophic rat retinae showed a robust outer nuclear layer (ONL) about 8–10 cells thick, while in non-operated dystrophic rats, this was reduced to an occasional cell lying in the outer border of the inner nuclear layer (FIG. 31). In sham-operated dystrophic rats it was usual to find a few photoreceptors around the injection site in the region of the disciform scar. By contrast, retinae that had received cell transplants, showed larger areas of photoreceptor survival which was as much as 6 cells thick close to the injection site while typically diminishing to 2 cells thick towards the nasal retina.

These results show that the SV40 large T antigen transfected human RPE cell line hRPE7, which in vitro exhibits phenotypic characteristics of RPE cells, supports photoreceptor survival and limits the deterioration of visual function for up to 5 months after transplantation into the subretinal space of RCS rats. In these cyclosporin-treated animals the grafted hRPE7 cells showed no evidence of inducing an overt inflammatory response. In addition, despite long-term immunosuppression, there was no evidence of uncontrolled growth.

In cell grafting strategies for clinical application, cell lines have the advantage that they can be easily tested for safety factors, such as retroviruses, and can be expanded as required. These important characteristics make them preferable to primary culture cells for transplantation. However the question of immune rejection has yet to be addressed by exploring the efficacy of strategies such as local immunosuppression, induction of tolerance and/or the further genetic engineering of the hRPE cells lines. While the subretinal space may be regarded as immunological privileged site Neiderkorn, 48 Adv. Immunol. 1208 (1990); Jiang et al., 58 Exp. Eye Res. 719 (1994)), it is clear that in the RCS rats, leaky vessels appear (Villegas-Perez et al., 392 J. Comp. Neurol. 58 (1998)), which may abrogate such privilege and there is clear evidence that allografts of primary cell cultures are subject to rejection (Zhang & Bok, 39 Invest. Ophthalmol. Vis. Sci. 102 (1998)). Similarly, in patients with AMD, it is likely that RPE cell transplants may also be rejected (Algvere et al., 232 Graefe's Arch. Clin. Exp. Ophthalmol. 707 (1994); Algvere et al., 235 Graefe's Arch. Clin. Exp. Ophthalmol. 149 (1997)).

In summary, the ability of a human RPE cell line to rescue visual function has been demonstrated in the RCS rat using physiological and behavioral tests which are analogous to those used to assess visual function in humans. The use of cell lines provides a potential and very valuable approach to prevention of retinal degeneration that seems practical to explore in humans.

EXAMPLE 12

Subretinal Transplantation of Spontaneously Immortalized Human RPE Cell Line Prevents Visual Loss in the RCS Rat The ARPE-19 cell line (Dunn et al., 62 Exp. Eye Res.155–69 (1996), Dunn et al., 39 Invest. Ophthalmol. Vis. Sci. 2744–9 (1998), Finnemann et al, 94 Proc. Natl. Acad. Sci. USA 12932–7 (1997), Handa et al., 66 Exp. Eye. 411–9 (1998), Holtkamp et al., 112 Clin. Exp. Immunol. 34–43 (1998), Maidji et at, 70 J. Virol. 8402–10 (1996)) is available from the American Type Culture Collection (ATCC Number CRL-2302). ARPE-19 cells are cultured in DMEM/F12 medium containing 10% heat-inactivated FBS. Cell transplantation into the subretinal space of 3-week-old RCS rats as well as optokinetic tests were performed according to the procedure described in EXAMPLE 11. Animals were tested 8 weeks postoperatively. A single operator conducted all assessments blind and codes were broken upon completion of all data acquisition. The effect of ARPE-19 on the optokinetic performance of the RCS rats was compared to that of sham and hRPE7 at 2 passages as well as to untreated dystrophic and non-dystrophic congenic rats (FIG. 32).

Analysis of head tracking performance revealed a significant distinction between graft and sham injected animals by 8 weeks postoperatively ($p<0.01$; FIG. 32). Behavioral data was analyzed using an analysis of variance (2-way ANOVA with repeated measures). Post-hoc analysis was performed on factors that were shown to be significant from the ANOVA.

By 8 weeks, dystrophic animals who received a transplant of hRPE7 or ARPE-19 were able to track the 0.125 cycles/° and 0.25 cycles/° grating stimuli and were significantly better than sham operated and non-operated dystrophic control animals (FIG. 32). At a grating of 0.125 cycles/° both cell types perform equally well whereas at 0.25 cycles/° ARPE-19 tend to be less effective than hRPE7 at passage 21. Interestingly, hRPE7 at passage 14 shows lowest performance at this grating stimulus. In conclusion, ARPE-19 transplanted animals were able to track visual stimuli at 8 weeks postoperatively in contrast to both sham operated and dystrophic animals. Its effect was somewhat less pronounced than seen for hRPE7.

The foregoing description has been presented only for the purposes of illustration and is not intended to limit the invention to the precise form disclosed, but by the claims appended hereto.

We claim:

1. The cell line IO/JG2/1, deposited under 1-1695 on Apr. 18, 1996 in the collection Nationale de Cultures de Microorganismes held by the Institut Pasteur, Paris, France.

* * * * *